(12) United States Patent
Schultz et al.

(10) Patent No.: US 8,829,428 B2
(45) Date of Patent: Sep. 9, 2014

(54) TIME-OF-FLIGHT SPECTROMETRY AND SPECTROSCOPY OF SURFACES

(75) Inventors: J. Albert Schultz, Houston, TX (US);
Thomas F. Egan, Houston, TX (US);
Steven Ulrich, Houston, TX (US);
Kelley L. Waters, Houston, TX (US)

(73) Assignee: Ionwerks, Inc., Houston, TX (US)

( * ) Notice: Subject to any disclaimer, the term of this patent is extended or adjusted under 35 U.S.C. 154(b) by 116 days.

(21) Appl. No.: 12/956,665

(22) Filed: Nov. 30, 2010

(65) Prior Publication Data

US 2011/0147578 A1 Jun. 23, 2011

Related U.S. Application Data

(60) Provisional application No. 61/264,897, filed on Nov. 30, 2009.

(51) Int. Cl.
*H01J 49/40* (2006.01)
*H01J 49/00* (2006.01)
*H01J 49/14* (2006.01)
*G01N 23/225* (2006.01)

(52) U.S. Cl.
CPC ........... *H01J 49/142* (2013.01); *H01J 49/0095* (2013.01); *H01J 49/0004* (2013.01); *G01N 23/2258* (2013.01)
USPC ............. 250/287; 250/281; 250/282

(58) Field of Classification Search
CPC ........................................................ H01J 49/40
USPC ............................................................. 250/287
See application file for complete search history.

(56) References Cited

U.S. PATENT DOCUMENTS

| | | | |
|---|---|---|---|
| 5,315,113 A * | 5/1994 | Larson et al. | 250/305 |
| 6,380,666 B1 | 4/2002 | Kawato | |
| 8,280,664 B2 * | 10/2012 | Kimba et al. | 702/95 |
| 2005/0006577 A1 | 1/2005 | Fuhrer et al. | |
| 2006/0289746 A1* | 12/2006 | Raznikov et al. | 250/294 |
| 2009/0189072 A1* | 7/2009 | Egan et al. | 250/287 |
| 2009/0309015 A1* | 12/2009 | Schultz et al. | 250/281 |

OTHER PUBLICATIONS

International Search Report and Written Opinion of the International Searching Authority, issued Mar. 22, 2011, from International Application No. PCT/US2010/58369.

* cited by examiner

*Primary Examiner* — Phillip A Johnston
(74) *Attorney, Agent, or Firm* — Fulbright & Jaworski LLP

(57) ABSTRACT

Described is an analytical method and apparatus for counting and measuring the flight time of secondary electrons, secondary ions and neutrals, scattered ions and/or neutrals and for correlating coincidences between these while maintaining a continuous un-pulsed, micro-focused, primary particle beam for impinging a surface for purposes of microprobe imaging and microanalysis.

37 Claims, 13 Drawing Sheets

TIME-OF-FLIGHT SPECTROMETRY AND SPECTROSCOPY OF SURFACES

CROSS-REFERENCE TO RELATED APPLICATIONS

This application claims priority to U.S. provisional patent application 61/264,897, filed Nov. 30, 2009.

STATEMENT REGARDING FEDERALLY SPONSORED RESEARCH OR DEVELOPMENT

This invention was developed in part, under Award NO. 0912355 from the National Science Foundation SBIR phase I small business program. The U.S. government may have rights in the invention.

TECHNICAL FIELD

The present invention generally relates to the fields of mass spectrometry and in particular the area of elemental surface analysis and imaging by mass spectrometry. Specifically, the invention concerns a method and apparatus for counting and measuring the flight time of secondary electrons, secondary ions and neutrals, scattered ions and/or neutrals and for correlating coincidences between these while maintaining a continuous, micro-focused, primary particle beam for impinging a surface for purposes of microprobe imaging and microanalysis in regions with diameters as small as nanometer dimensions.

BACKGROUND OF THE INVENTION

Ion beams have been used as probes in TOF (Time-of-Flight) mass spectroscopy of surfaces of material for years (Hammond et al., 1995). Imaging and elemental analysis by energy analysis of the backscattered ions and backscattered neutrals and forward recoiled elemental ions and neutrals created during the collisions between incident ions and surfaces can yield information on both surface structure and composition. Moreover, by scanning a Focused Ion Beams (FIB) and recording the secondary particle intensity as a function of beam location, images have been obtained of surfaces as diverse as semiconductor and biological surfaces. Secondary particles such as secondary electrons, secondary ions sputtered from the surface, and (less so) backscatter ions and neutrals have all been employed. The fundamental limitation preventing FIB imaging being as useful as secondary electron microscopy is only partly due to the inability to focus the ion microprobe to nanometer dimensions. More significant is the difficulty to capture a significant fraction of the diffuse secondary particle emission released during ion bombardment of the surface. Analyzing the energy and masses of these secondary particles with sufficient resolution in a time scale fast enough for rapid FIB surface imaging is yet another.

An example of these limitations of the prior art is to be seen for the specific case of ion (and neutral) backscattering and surface recoil analysis; however the limitation in this area which we will now discuss also transfer to the use of other secondary species for obtaining image contrast during microprobe surface imaging. Measuring the energy loss of the backscattered primary ions/neutrals generated when an KeV ion beam strikes the surface of a material has been used extensively for elemental and structural analysis of the surface for the last 25 years. The Co-Axial Impact Collision Ion Scattering Spectrometry (CAICISS) (Katayama et al., 1988 and Aono et al., 1992) technique (FIG. 1) is a special case of low energy Rutherford Backscattering which measures energy losses of backscattering Helium atoms and Helium ions when a nanosecond pulsed Helium ion beam impinges a surface. The energies of the backscattered Helium are determined by measuring their time of flight from the sample to the detector. The backscatter time of flight from the sample to the detector is relative to the time at which the Helium ion beam is initially pulsed. Since the mass of Helium is known and the length and geometry from the ion source to the sample and the sample to the detector are well-defined, the energy loss of each Helium atom arriving at the detector can be computed. The energy will be high (fast time of flight) when the Helium backscatters from a heavy element and low when it strikes a light element (slow time of flight). It is important to note when using ion scattering spectrometries—most primary ions neutralize as they closely approach the surface and remain neutralized as the primary particles backscatter from the surface. However, the velocity of Helium at a few hundred eV is still large enough to generate a substantial signal on a time of flight particle detector; therefore, the neutral helium can be detected and its time of flight measured. Thus most of the Helium which backscatters from the surface into an angle subtended by a backscatter particle detector can be used irrespective of its charge state.

We will now discuss other limits, some fundamental and some technical, to the elemental mass specificity of backscattering techniques. For example the physical scale of these instruments is a huge drawback. The beam-line and backscattering detector are over a meter in length. The actual flight path for the backscattered ions/neutrals is about 500 millimeters (mm); this path length is necessary to obtain an acceptable spectrum when the pulse duration of Helium is tens of nanoseconds. As seen in FIG. 1 (prior art) and FIG. 2 (illustrating the prior art juxtaposed against an embodiment of the present invention), the angle subtended by a 40 millimeters diameter detector is very small (approximately a two degree half angle) because of this large geometry. A further drawback to imaging is the rather large (a few hundred micron diameter) spatial focus of the ion beam on the sample.

Fundamental limitations also exist for detecting light elements, such as Oxygen. Light elements are detected poorly by Helium backscatter relative to heavier elements, such as Zinc (FIG. 3). This is because of higher scattering cross-sections of He from Zn compared to O and also because the He scattering from O is at a longer time which occurs on the straggling tail of the more intense He scatter from Zn. FIG. 3 shows two overlapped spectra from 2 keV Helium backscattering from a ZnO single crystal (Aono et al., 1992). In spectrum (b) the sample surface was tilted by 68 degrees from the Helium beam. The Helium scattered from Zinc is well resolved but no signal from Oxygen is observed. By contrast in spectrum (a) when the beam impinges the surface at 0 degrees incidence (normal to the surface), the backscatter from Zinc is no longer well resolved since a direct hit by the primary Helium onto the Zinc is blocked by a surface Oxygen. However Helium scatter from the surface Oxygen is not seen in either (a) or (b), simply because the cross-section for Helium backscatter decreases is significantly less than from Zn. It is thus desirable to combine backscattering with forward recoil detection by placing one or more detectors in the forward scattering direction so that the energy of light recoiled surface elements can be simultaneously determined.

Another example and application of CAICISS is monitoring film growth. However, elements which are close in mass such as Lanthanum (La) and Strontium (Sr) are difficult to resolve by backscatter due to nearly equal Helium backscatter flight times from each. Moreover, depending on the azimuthal scattering angle (angle by which the surface is rotated around its normal), the scattering signal intensities can vary significantly. The variation in signal intensity depends on scattering from heavy species like La or Sr compared to the lighter material like Manganese. Also, the variation in signal intensity depends on the surface structure (where each element is shadowing and blocking its nearest neighbor at certain angles). FIG. 4A shows the Helium Time-of-Flight backscatter spectra obtained with the beam incident at 55° (elevation above the surface plane is 35°) to determine the geometric structure of the surface by the use of backscattered Helium (Ohnishi et al., 1998). The dependence of the scattered Helium intensity on the azimuthal angle is shown in FIG. 4B. The signal intensities can vary significantly depending on the azimuthal scattering angle, the scattering from heavy species like La or Sr versus lighter materials like Manganese and depending on the surface structure (where each element is shadowing and blocking its nearest neighbor at certain angles). The azimuthal angle and/or elevation scanning (rotation and/or tilting) of the sample relative to the Helium beam incidence plane can clearly be used to provide information regarding local surface crystallography and these techniques yield local geometries which cannot be measured by more long-wavelength diffraction techniques such as electron or x-ray diffraction. However, the practical use of this technique is limited by the time necessary to turn the sample and record intensity variations into a small angular acceptance backscatter detector. While this problem has been partly addressed in the prior art by using large acceptance angle position sensitive detectors which reduces the need for some of the sample adjustments, such devices still remain relatively large, slow, and cumbersome.

The variance in backscattering intensities as a function of atomic number (Z) in (FIGS. 4A and 4B) would be lower from this sample if a Neon primary ion beam were used since the overall variance of Neon backscatter cross-sections is less as a function of atomic number (Z); however, Neon cannot backscatter from any element lighter than itself, which precludes any backscattering from first row elements such as Fluorine. However, the lighter elements are efficiently forward recoiled by the Neon towards the surface. The forward recoiled lighter elements then scatter backwards and/or sideways from their heavier nearest neighbors and the lighter elements arrive at the backscatter detector with keV type energies and flight times which are faster than the backscattered Neon. However, not much practical use has been made of this phenomenon other than to study the essential physics of the multiple atom collision sequences involved. An alternative has been to tilt the sample relative to the incident ion beam and to position a position sensitive detector to intercept forward recoiled surface atoms and ions and forward scattered primary particles.

Another aspect involves Secondary Ion Mass Spectrometry (SIMS) imaging of surfaces, combined with secondary electron detection and ion scattering. Spatially resolved microprobe images of the surface are routinely obtained by measuring and recording the variation of the secondary electron yield as a micro-focused energetic primary particle beam (such as an electron, ion, photon is scanned from one micro-focused point on the surface to the next. While the previous discussion focused on combining ion backscattering experiments into an ion microprobe which also can image a surface by detecting secondary electrons, it is well known that other ejection processes simultaneously occur when a focused energetic primary particle beam (photon, electron, ion) strikes the surface. Extremely useful elemental and molecular images of the surface may be obtained by simultaneously using other contrast mechanisms to augment the secondary electron images. For example other images can be obtained using the intensity, the energy and/or the mass of secondary ejected particles. The secondary ejected particles include but are not limited to photons, backscattered primary particles, secondary ions directly created and sputtered by the incoming primary particle beam, or secondary ions created by photo-ionizing secondary sputtered neutral elements or molecules. The sputtering of secondary neutrals is often the most predominant sputtering channel for many elements and molecules on the surface. Focused ion beams have been also used with SIMS for elemental and molecular analysis and imaging of these surfaces using magnetic, time-of flight, or orthogonal time of flight mass spectrometers; however prior art mass spectrometers are necessarily large in order to obtain the high mass resolution necessary to identify secondary elemental ions from secondary molecular ions which directly conflicts with the needs of microprobe imaging for fast scanning from one micropixel to the next on the surface in order to obtain the image in the shortest time possible. The need for large, high mass resolution mass spectrometers with bulky secondary ion extraction optics also conflicts directly with the necessity for the micro-focusing primary beam optics to also be as close as possible to the sample. The long flight time of secondary particles through large secondary particle analysis instrumentation is an ever-present conflict with the stringent requirements of surface imaging—namely, during imaging it is imperative to quickly move the position of the micro-focused primary particle from one surface location to the next while recording the intensity of the secondary particles as quickly as possible.

The present invention provides a detector suite for correlating some or all such coincident and non co-incident secondary particle emissions to simultaneously obtain primary particle beam microprobe spatial imaging. Each of the different types of secondary particles is detected either singly or in parallel and their intensities and co-incidences are recorded as the focused microprobe is scanned over the surface from one location to the next.

BRIEF SUMMARY OF THE INVENTION

The present invention provides particle detectors for counting and measuring the flight time of secondary species and to optionally correlate coincidences between and within secondary species and backscattered ions/and neutrals while maintaining the optimum focus of the microprobe. The unique configurations and implementation of these detectors achieve the necessary time of flight analysis during time frames which enables the use of a continuous (unpulsed), micro-focused primary particle beam for impinging a surface while still performing hybrid configurations of time of flight, ion mobility, electrostatic and magnetic separations of ions, and postionization of neutrals. Intensities of the primary particle scattering and other secondary particle emissions are correlated with the position of impact of individual primary particles which are focused onto the surface of a material. A spatially resolved surface elemental and electronic structural mapping is obtained by scanning the focused beam across the surface. Special features of the detectors and there operation will be described which also optimize techniques for post-ionization of secondary neutrals.

In one aspect of the present invention, there is a method for analyzing a sample comprising: generating a continuous micro-focused beam of primary species; directing the micro-focused beam of primary species to a sample and causing secondary species to be emitted from the sample; detecting the secondary species, wherein the step of detecting the secondary species comprises applying opposed electric fields proximate to the sample surface, the opposed electric fields having an axis or plane of symmetry about the micro-focused beam of primary ions, the opposed electric fields simultaneously directing secondary species in the form of positive ions to a first detector and directing secondary species in the form of negative ions and electrons to a second detector.

In one embodiment, the method further comprises the step of applying a magnetic field to the negative ions and electrons to create separated beams of the negative ions and electrons. In some embodiments wherein a magnetic field is applied to the negative ions and electrons, the method further comprises the step of detecting the beam of electrons with a detector. In some embodiments, the step of detecting said beam of electrons comprises counting individual electrons. In some embodiments, the further comprises measuring a timing signal from the step of counting. In some embodiments wherein individual electrons are counted, the method further comprises the step of using the step of counting individual electrons to establish the time of arrival of a primary ion at the sample. In some embodiments, the method further comprises the steps of determining the yield of the electrons at the detector and correlating the yield with a location of impact of the primary ions with the sample.

In some embodiments, the method further comprises the step of directing the positive ions, the negative ions or both the positive ions and the negative ions to a mass spectrometer. In such cases, the mass spectrometer may be a time-of-flight mass spectrometer. In those cases wherein a time-of-flight mass spectrometer is used, the time-of-flight mass spectrometer may be a orthogonal time-of-flight mass spectrometer (oTOFMS). In some embodiments, the mass spectrometer comprises a magnetic separator. In some embodiments, the mass spectrometer comprises a position sensitive detector. In some of the embodiments which use a magnetic separator, the magnetic separator comprises a rare earth magnet.

In some embodiments, the method further comprises the step of intermittently firing a photon source across an area above the surface of the sample to intersect secondary species emitted from the sample. In some of the embodiments in which a photon source is intermittently fired across an area above the surface of the sample, the method further comprises applying a local gas pressure of from $10^{-1}$ to $10^{-8}$ Torr in the region above the primary species impact location on the surface of the sample. In some embodiments, the method further comprises the step of applying a voltage pulse to extract positive and negative ions into the first and second detectors.

In some embodiments of the method, one or both of the first and second detectors comprise a mass spectrometer. In some embodiments, one or both of the first and second detectors comprise an ion mobility cell and, optionally, an oTOFMS mass spectrometer.

In one embodiment of the method, the step of directing the micro-focused beam comprises directing the micro-focused beam of primary species through an aperture in a position sensitive detector to a primary species impact location on a surface of the sample thereby creating backscattered primary species and secondary species, wherein the position sensitive detector is positioned relative to the sample, such that the minimum distance between the detector plane and the impact location of the primary species on the sample is less than or equal to 100 mm; and method further comprises: detecting, at the position sensitive detector, the backscattered primary species and the secondary species, including arrival time and impact location of the backscattered primary species and the secondary species on the detector; measuring a first timing signal wherein the first timing signal is generated when a first subset of secondary species strikes the position sensitive detector, the first subset of secondary species selected from the group consisting of electrons, photons, hydrogen atoms, hydrogen ions, and any combination thereof, and deriving a primary species impact time from the first timing signal, the primary species impact time being the time when the primary species impacts the sample; measuring a second timing signal wherein the second timing signal is generated when a second subset of secondary species strikes the position sensitive detector, wherein the second subset of secondary species is any secondary species other electrons, or any combination of secondary species other than electrons; and, calculating the times of flight for the secondary species and the backscattered primary species with a time of flight analysis using the first timing signal, the primary species impact location, the second timing signal, the impact position on the position sensitive detector, and a known geometry between the sample and the position sensitive detector. In some embodiments, the method further comprises the step of adjusting the micro-focused primary species beam fluence such that about only one particle hits the sample surface within a period between 100 nanoseconds and 10 microseconds. In some embodiments, the method further comprises the step of adjusting the micro-focused ion beam fluence such that about only one particle hits the sample surface within about 1 microsecond. In some embodiments, the method further comprises the step of accelerating the secondary species from the sample to the detector by applying an electric field between the sample and the detector. In some embodiments, the position sensitive detector is positioned relative to the sample, such that the minimum distance between the detector plane and the impact location of the primary species on the sample is less than or equal to 80 mm. In some embodiments, the position sensitive detector is positioned relative to the sample, such that the minimum distance between the detector plane and the impact location of the primary species on the sample is less than or equal to 50 mm. In some embodiments, the position sensitive detector is positioned relative to the sample, such that the minimum distance between the detector plane and the impact location of the primary species on the sample is less than or equal to 25 mm. In some embodiments, the position sensitive detector is positioned relative to the sample, such that the minimum distance between the detector plane and the impact location of the primary species on the sample is less than or equal to 10 mm. In a preferred embodiment, the position sensitive detector is positioned relative to the sample, such that the minimum distance between the detector plane and the impact location of the primary species on the sample is 5 mm. In some embodiments, the position sensitive detector is positioned relative to the sample, such that the minimum distance between the detector plane and the impact location of the primary species on the sample is 3 mm. In some embodiments, the method further comprises the steps of determining the yield of the secondary species and correlating the yield with a location of impact of said primary ions with the sample. In some embodiments wherein the yield of secondary species is determined and correlated with the impact location, the method further comprises the step of directing at least a portion of the secondary species to a mass spectrometer. In some embodiments, the mass spectrometer is a time-of-flight mass spectrometer. In some embodiments, the time-of-flight mass spectrometer is a orthogonal time-of-flight mass spectrometer. In some embodiments and Ion Mobilty is combined with the orthogonal time of flight mass spectrometer.

In another aspect of the present invention, there is an apparatus comprising: a source of a micro-focused beam of primary species; a surface for holding, rotating, and titling a sample, the surface positioned such that flow from the source is incident upon the sample; a plurality of electrodes, proximate to the sample surface and configured to produce two opposed electric fields to simultaneously direct secondary species in the form of positive ions in a first direction and to direct secondary species in the form of negative ions and electrons in a second direction, wherein the first and second directions are symmetrically opposed to one another about the primary ion beam; and, a first detector and a second detector, the first detector positioned to detect the positive ions travelling in the first direction, the second detector positioned to detect the negative ions and electrons travelling in the second direction. In some embodiments, the further comprises a magnetic separator positioned between the sample and the second detector. In some embodiments, the apparatus further comprises a magnetic field generating component to generate a magnetic field between the sample surface and the second detector. In some embodiments, the apparatus further comprises a secondary electron detector positioned between the sample and the second detector. In some embodiments, one or both of the first and second detectors comprise a mass spectrometer. In some embodiments comprising a mass spectrometer, the mass spectrometer is an orthogonal time-of-flight mass spectrometer, a magnetic spectrometer, or a combination of an orthogonal time-of-flight mass spectrometer and a magnetic spectrometer. In some embodiments in which the apparatus comprises a magnetic spectrometer, the magnetic spectrometer comprises a rare earth magnet. In some embodiments the magnetic spectrometer and Ion Mobilty is combined with the orthogonal time of flight mass spectrometer.

In some embodiments of the apparatus, one or both of the first and second detectors comprise an ion mobility cell combined with an orthogonal time of flight mass spectrometer. In some embodiments, the apparatus further comprises a photon source positioned to emit photons across an area above the surface of the sample. In some embodiments, the apparatus further comprises a gas doser positioned to apply from $10^{-1}$ to $10^{-8}$ Torr of gas pressure in the region above the primary species impact location on the surface of the sample.

In some embodiments, the apparatus further comprises an electron source positioned between the first detector and the sample.

In some embodiments, the apparatus further comprises: at least one position sensitive detector, the position sensitive detector positioned to detect backscattered primary and secondary species.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

It is readily apparent to the skilled artisan that various embodiments and modifications can be made to the invention disclosed in this Application without departing from the scope and spirit of the invention.

As used herein "a" or "an" means one or more than one unless expressly stated to the contrary or otherwise clear from the context. For example, reference to "a species" means one species or more than one species.

As used herein "primary species" or "primary particle" is defined as energetic particles used to impinge a sample. Such primary species can be a photon, a charged or neutral atomic, molecular, nanoparticulate, or cluster of elements of any kind and any combination thereof.

As used herein "secondary species" or "secondary particle" is defined as electrons, photons, recoiled atoms, recoiled ions (both atomic and molecular), recoiled molecules, sputtered atoms, sputtered molecules, sputtered ions (both atomic and molecular), backscattered atoms, backscattered molecules, backscattered ions (both atomic and molecular), clusters of any kind, and any combination thereof. The term "secondary species" or "secondary particles" refers to the material ejection that results during and immediately after the collision of a primary species with a sample.

As used herein "MALDI" refers to matrix assisted laser desorption/ionization which can be accomplished using nanoparticulate matrices.

Figure 1:
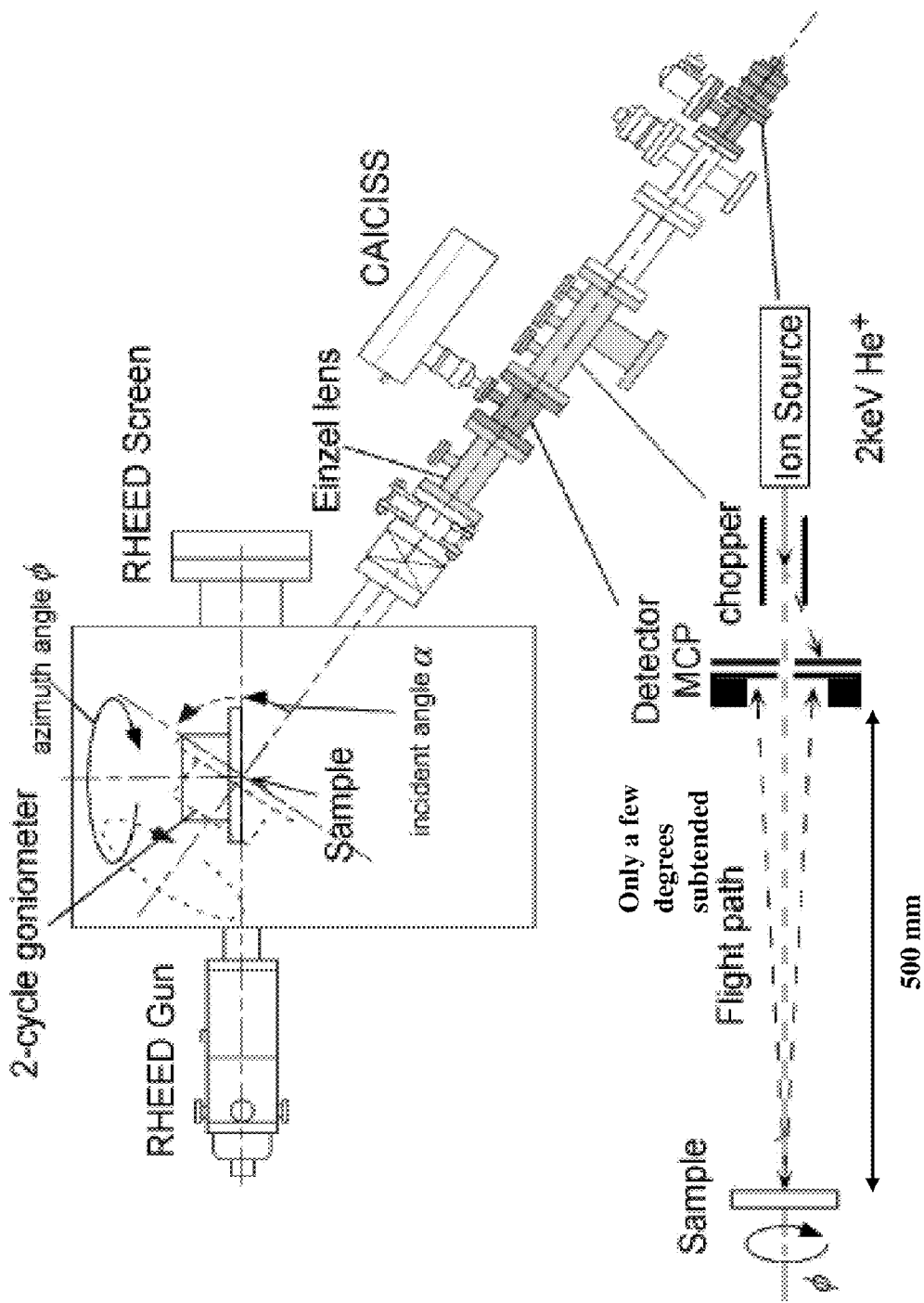
FIG. 1 shows an example of a prior art CAICISS instrument for He backscatter.

An example of a prior art CAICISS instrument can be found in FIG. 1. In the CAICISS technique, the elemental composition of a surface is determined by pulsing ("chopping") a mono-energetic Helium (He) ion beam of moderate spatial focus so that a packet of ions hits the surface all within a few nanoseconds. Since the individual Helium ions will lose a specific amount of energy when it backscatters from a particular element, it is then possible to collect and interpret the information regarding the elemental composition of a surface. The elemental composition is determined by evaluating the loss peaks in a Helium time-of-flight spectrum in which the loss peaks correlate with the Helium arrival times at backscatter detector. If the Helium strikes a heavier element, then the Helium loses very little energy and comes back to the detector quickly. However, if the Helium strikes a lighter element then more energy is lost by the Helium during the collision and the Helium backscatters from the lighter element with a slower velocity.

Typically, a monoenergetic continuous He beam of a few KeV is generated in the ion source. The "chopper" electronically deflects this continuous Helium ion beam across a slit so that only a small number of ions is allowed to pass through the slit/detector within a few nanoseconds and then the ions travel on to the sample; however, the process of pulsing the beam and the dimensions and geometric restraints on the helium primary ion beam focusing prohibits focal spots on the sample of less than a millimeter. A timing circuit, typically a time to digital converter (TDC), is enabled as the continuous helium beam is electronically deflected across a slit located just behind the backscatter detector. Thus the timing of the pulsed ion bunch of Helium ions starts as they exit the slit in the backscatter detector and ends after they have impacted atoms on the surface of the target, backscattered towards the coaxial backscatter detector each with a specific range of velocities depending on the type and local geometry surrounding the atomic elements on the surface, and the TDC records an electronic signal as either each ion or (most likely) each fast helium neutral impacts the detector surface. The flight time of the helium primary ion between the slit and the sample can be can be accurately calculated using the known distance between the pulsing slit and the sample surface and the known energy of the near monoenergetic primary helium ion. The backscatter flight time of the helium ion or neutral recoiling from the surface into the backscatter detector can then be obtained by subtraction of the primary ion flight time to the sample from the total time measured by the TDC between the pulse formation event and the ultimate detection of a backscattered primary particle returning to the backscatter detector. This time zero measurement can be further refined by recording the total backscatter times from several standard structures containing known compositions and structures of surface elements. The backscatter times can be converted to backscatter energies from these measured times and known distance from the sample to the backscatter detector. The energies of the backscattered particles are then related to the presence of atoms of a certain mass on the surface.

Figure 2:
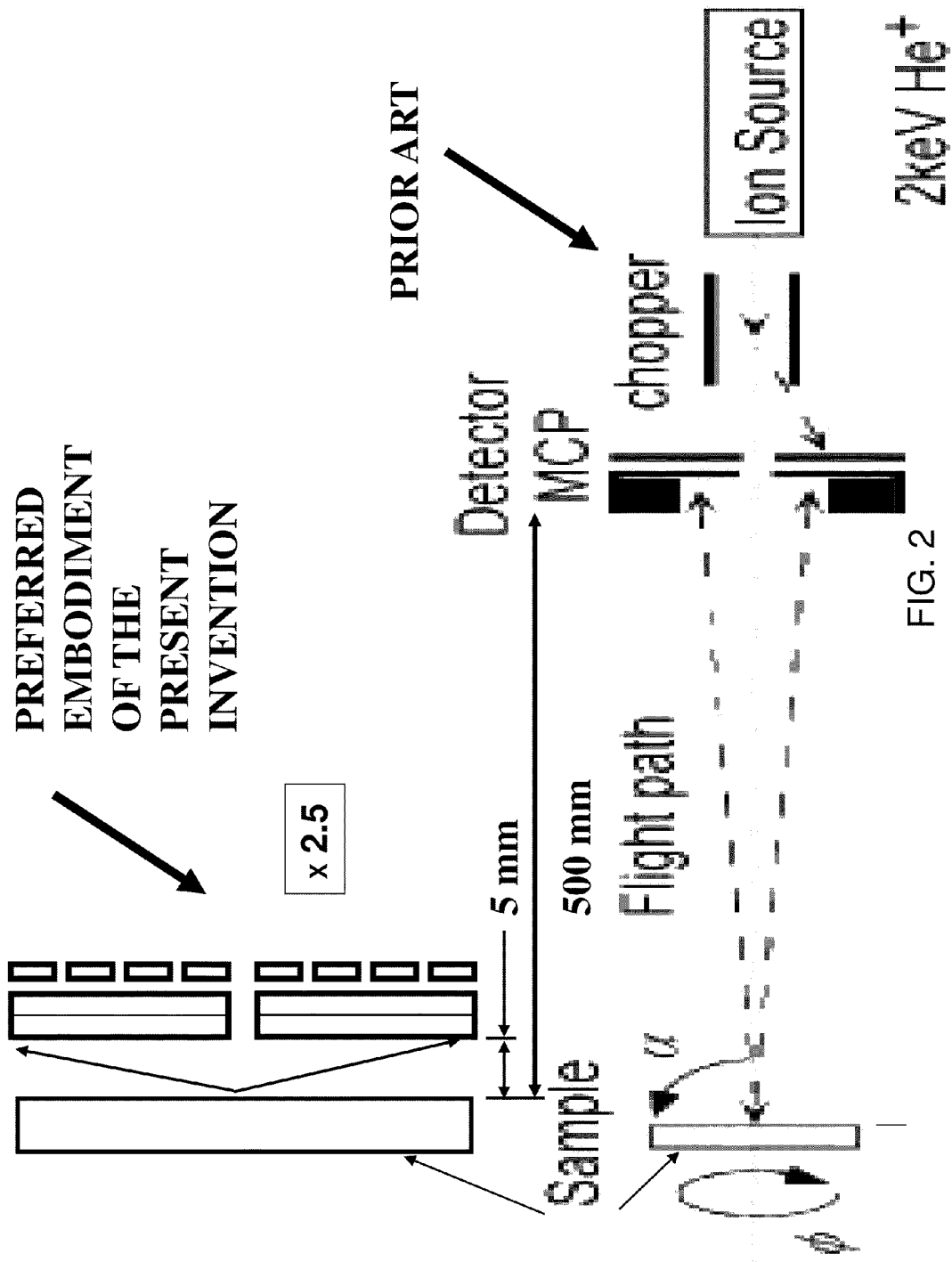
FIG. 2 compares the dimension of prior art backscatter with a preferred backscatter detector embodiment.
Figures 4A, 4B:
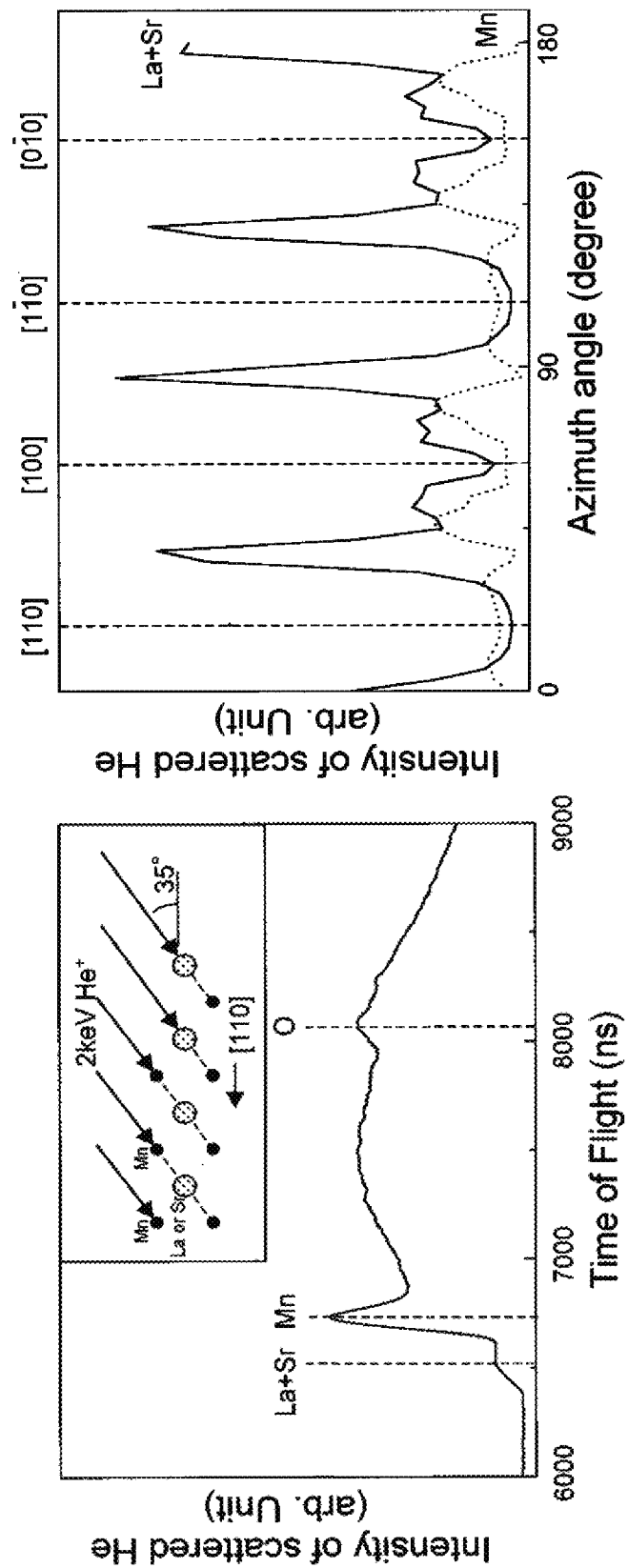
FIG. 4A shows CAICISS-TOF spectrum recorded at the incident angle of 55° along azimuth for the $La_{0.7}Sr_{0.3}MnO_3$ film surface.
FIG. 4B shows the Azimuth angle dependence of (La+Sr) and Mn signal intensities at the incident angle of 55° for the $La_{0.7}Sr_{0.3}MnO_3$ film surface.
Figure 5:
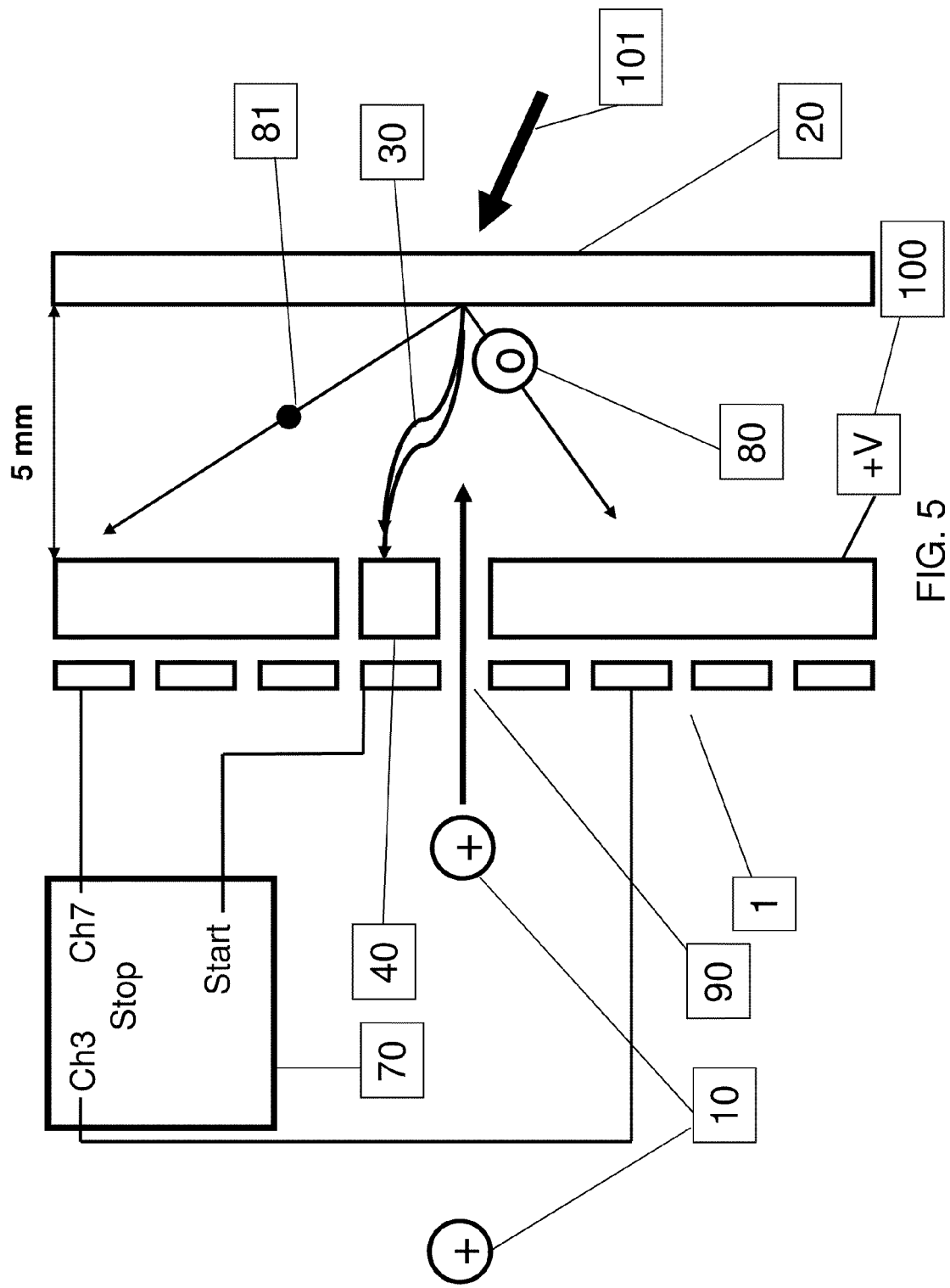
FIG. 5 shows the angle and time resolved backscatter particle detector.

When the Helium packet strikes the sample, most of the Helium ions are neutralized. Some of the resulting neutral Helium atoms (and surviving ions) will backscatter from either a binary collision between the helium ion and a single surface atom or by multiple collisions (with high probability) between the helium ion and several of the nearest neighbors around the first struck surface atom. In comparing the collision between a primary Helium ion and a heavy surface atom to the collision between a second Helium ion and a light surface atom, the energy loss of the primary helium is less when colliding with a heavy surface atom; therefore, the time of flight of the Helium to the detector will be faster when Helium collides with an element such as Au than when Helium collides with a lighter element such as Li. Even in the case of collisions with light elements, the backscattered Helium species have sufficient velocity to be recorded by the detector. Thus repeated pulsing of the beam and collecting the times of flight of each of the backscattered Helium species will result in a spectrum which measures the presence of different elements on the surface (see FIGS. 2-4). Note the large scale (500 mm) of the prior art CAICISS instrument in FIG. 1 and the small angle (only a few degrees) subtended by the detector (as shown in the schematic located under the instrumental cross-section in FIG. 1). Also, in FIG. 2 is demonstrated one improvement realized by the present invention, with the angle subtended being much larger (the example in FIG. 1 shows 120°, although other angles, both smaller and larger, are possible), and flight path being only 5 mm (although more broadly, in the present invention the flight path is less than or equal to 100 mm, less than or equal to 80 mm, less than or equal to 50 mm, less than or equal to 25 mm, less than or equal to 10 mm, and preferably equal to 5 mm or equal to 3 mm). FIG. 2 juxtaposes the prior art instrumental platforms (bottom) with the preferred embodiment of the present invention (top). This feature of scale of the present invention is also illustrated in FIG. 5. At each distance the sample can be rotated or tilted about the focal spot at which the primary microprobe impinges the sample so that forward and backscatter angles can be viewed by different types of secondary particle detectors.

One of the most general embodiments of the timing and position sensitive backscatter detector (1) is seen in the FIG. 5 cross-sectional view. Note the path-length scale difference (5 millimeters compared to 500 millimeters) and that the backscatter angle subtended by the detector (1) will now be over 120 degrees compared with only a few degrees for the CAICISS technique (see also FIG. 2). Longer flight paths are not needed in order to obtain accurate backscatter spectra as long as the time at which the primary ion (10) collides with the sample surface (20) can be determined within a few hundred picoseconds or less using the secondary electrons (30) generated in the collision and collected by the secondary electron detector (SED) (40). The timing precision and small scale aspect of the present invention has heretofore not been recognized or appreciated in the art. This high timing accuracy sensing of the primary ion (10) arrival at the surface (20) is accomplished by collecting individual secondary electrons (30) which are generated when the primary ion (10) strikes the surface are using the secondary electron detector (SED) (40) which produces an electronic timing start signal which is presented to the "start" input of a multichannel TDC (70). This timing start signal essentially replaces the beam chopping of prior art instruments and allows picosecond timing resolution, not only of the subsequent backscattered primary ions (80) but of any subsequent other secondary species scattered or emitted from the surface and arriving at the position sensitive backscatter detector (1). Thus, In addition to detecting backscattered particles [80], the user may record multiple collision sequences involving several atomic collisions between primary particles and surface atoms which, in addition to producing backscattered particles, also liberate electrons photons, and sputter secondary ions as well as recoiled surface atoms (81) with keV energies. Also an important coincident sequence involves multiple collisions which can liberate all light (as well as heavy elements) from the surface as recoils which can exit to the detector. The device described herein can be used to uniquely count the number of secondary electrons (30) generated in the collision which allows recording the exact number of secondary electrons (30) from each primary ion collision (10).

In the embodiment shown in FIG. 5, the micro-focused primary ions enter through a hole 90 in the backscatter detector which can generate an accurate position and timing signal which is presented to one of the stop channels. The secondary electrons produce a start signal which indicates that one micro-focused primary ion (Helium in this figure) has hit the surface. A weak electric field (100) (of between 0.5 volt/cm to 1 kvolt/cm between the sample and the detector) accelerates the secondary electrons from the sample to the detector and the flight times are on the order of 0.6 nanoseconds with a 300 picosecond spread (without magnetic field) and 30 picoseconds with the magnetic (B) field (101). In some embodiments, the magnetic field is not necessary since the highest timing resolution is not required. Some additional and/or alternate embodiments do not require the directing of the secondary electrons using the magnetic field to specific anode regions. Omission of the magnetic field certainly simplifies the construction and operation of the detector but decreases the likely capture of some of the secondary electrons. Both low and high timing resolution (without or with magnetic field) in this instrument can resolve elemental backscatters with resolutions comparable to or exceeding that seen in FIGS. 2-4 from the much larger conventional instrument.

Table 1 and Table 2 provide calculated times of flight for backscattering of Helium (or Neon) from chosen examples of heavy and light elements. For insulating materials the primary beam quickly charges the surface which can deflect the position and focus of the primary beam (as well as any secondary electrons liberated). This problem may be minimized or eliminated by the application of a low energy flood of electrons which neutralize the charged surface. In some embodiments, this neutralization process can be controlled and used in conjunction with the detector since the number of electrons is being accurately measured for each ion impingement. This allows for the surface to be maintained electrically neutral by replenishing electrons to the surface from a separate electron source. For imaging metals and semiconductors, it is usually not necessary to use an electron flood, as surface charging is not typically a problem for such materials.

The present invention provides a device that allows the use of a continuous micro-focused ion beam. The spot size and low beam currents of micro-focused ion beams are well suited to ensure that the average time between primary particle impacts on the surface is more than several hundred nanoseconds, so there is no need to pulse the beam and subsequently ruin the spot size of the micro-focusing since all the time of flight particles scatter and recoil.

Angularly Resolved Backscattering

The flight times of the secondary electrons (30) from the sample (20) to the SED detector (40) are on the order of around 2 nanoseconds with a 300 picosecond spread (even without magnetic field). The beam fluence is preferably adjusted so that on average, only one ion (10) hits within a 1 microsecond window. The average number of ions per unit time arriving at the surface may be calculated using industry standard techniques. For example, a micro-focused ion beam is often operated at or below 100 femtoamperes. One hundred femtoamperes is equal to $100 \times 10^{-15}$ coulombs/second and the charge on each ion is $1.6 \times 10^{-19}$ coulomb/ion. By dividing the charge per ion by the charge per second, it is determined that the average number of microseconds per ion is 1.6. This example is not limiting, and based on this disclosure, the skilled artisan will readily recognize alternative methods for calculating the average number of ions per unit time arriving

TABLE 1**

| Element Scattered from in the surface (amu) | 163.3° scattering angle | | 122° scattering angle | |
| --- | --- | --- | --- | --- |
| | $E_{backscattered\ Helium}$ (keV) | TOF (nanoseconds) | $E_{backscattered\ Helium}$ (keV) | TOF (nanosecond) |
| Carbon (12) | 5142.9 | 10.4797 | 6889.7 | 16.3567 |
| Arsenic (75) | 16227.3 | 5.8997 | 16985.6 | 10.4173 |
| Indium (115) | 17452.4 | 5.6889 | 17979.9 | 10.1252 |
| Gold (197) | 18471.3 | 5.5298 | 18795.1 | 9.9032 |

**20 keV He+ micro-focused onto a sample will backscatter with the above Energies and TOF into Detector 5 millimeters away.

TABLE 2++

| Element Scattered from in the surface (amu) | 163.3° scattering angle | | 122° scattering angle | |
| --- | --- | --- | --- | --- |
| | $E_{backscattered}$ (keV) | TOF (µsec) | $E_{backscattered}$ (keV) | TOF (µsec) |
| Carbon (12) | 1452.0 | 0.0441017 | FORBIDDEN | — |
| Arsenic (75) | 6856.3 | 0.0202953 | 8645.0 | 0.0326511 |
| Indium (115) | 10050.4 | 0.0167629 | 11674.8 | 0.0280968 |
| Gold (197) | 13420.8 | 0.0145062 | 14641.8 | 0.0250891 |

++20 keV Ne+ micro-focused onto a sample will backscatter with the following Energies and TIME-OF-FLIGHT into Detector 5 millimeters away at the surface without deviating from the spirit and scope of the present invention. Thus, the probability that a second primary ion will hit within the backscatter time of flight of the first ion (e.g. 50 nanoseconds) is extremely small and can always be made smaller by reducing the ion (10) current. Imaging is often performed with 10 femtoamps of beam current in which case the average time between ions is 16 microseconds. The small percentage of ions (10) which do overlap in a time within the backscattering time frame can be ignored since these will on average contribute a small random background which will be distributed over all times and angles.

Addition of Focusing Magnetic Field

Figure 3:
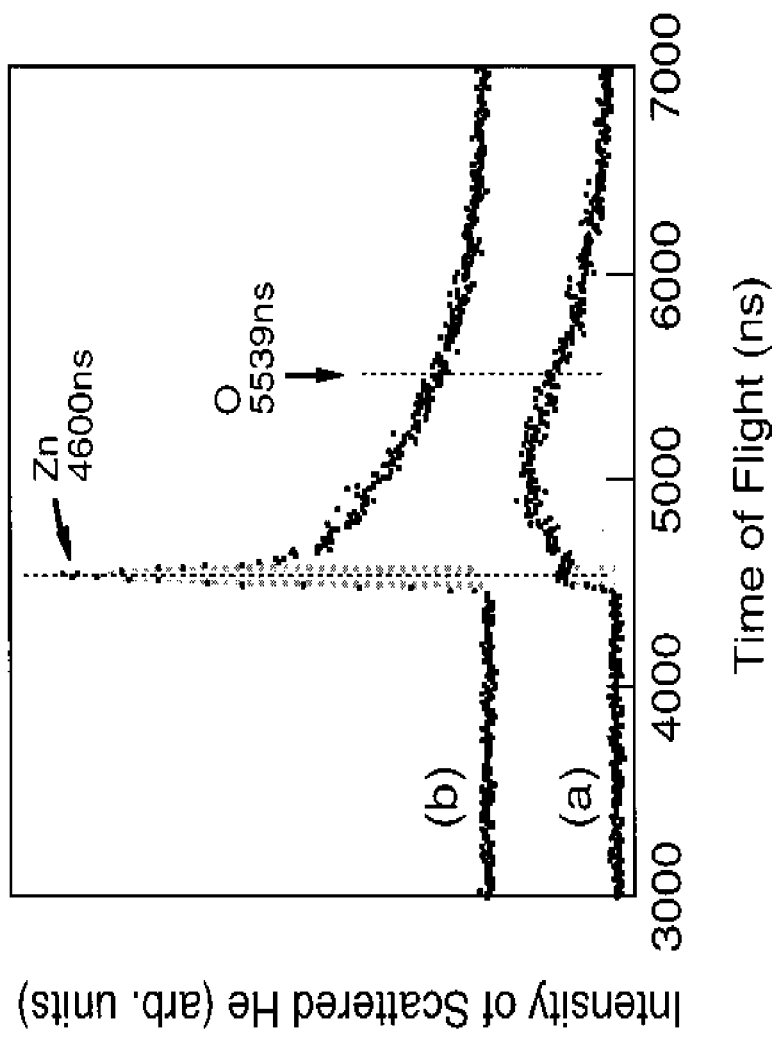
FIG. 3 shows a Time-Of-Flight backscatter spectra from the surface of a ZnO single crystal.

A weak electric field (of between 0.5 volt/cm to 1 kvolt/cm between the sample and the detector) accelerates the secondary electrons from the sample to the detector and the flight times are on the order of 0.6 nanoseconds with a 300 picosecond spread (without magnetic field) and 30 picoseconds with the magnetic (B) field as seen in table 3. In some embodiments, the magnetic field is not necessary since the highest timing resolution is not required. Some additional and/or alternate embodiments do not require the directing of the secondary electrons using the magnetic field to specific anode regions. Omission of the magnetic field certainly simplifies the construction and operation of the detector but decreases the likely capture of some of the secondary electrons. Additionally, the lack of magnetic field reduces the beam damage necessary to obtain an ion induced secondary image. More importantly the magnetic field allows the electron yield to be determined for each and every collision. By correlating the co-incidence of the backscatter with the electron yields, a differential yield of secondary electrons can be shown to originate in regions of the crystallite which contains atoms that were identified by the backscatter experiment. This type correlation among other coincident particles is also possible. It is possible to detect and identify the recoiled surface elements because the recoiled surface elements are in co-incidence with the electrons. Both low and high timing resolution (without or with magnetic field) can resolve elemental backscatters with resolutions comparable to or exceeding those from the larger conventional instrument as seen in FIGS. 2-4. Tables 1 and 2 give some calculated times of flight for the backscattering of Helium (or Neon) from heavy and light elements.

The magnetic field and localization of all secondary electrons into one region allows a number of advantages: 1) sub-50 picosecond timing resolution of the impact time of the primary particle, 2) digital timing and counting of the number of electrons ejected in each collision by constructing multiple anodes behind the region of the MCP where the electrons are focused, or digital counting and timing of the number of electrons passing through an alternative second hole in the MCP so that electrons pass through to a multichannel dynode or multichannel "channeltron" type electron multiplier, 3) precisely measuring the time interval between successive primary ion arrivals which allows the use of transforms for certain applications or for numerically excluding any false coincidences 4) determining the number of electrons which have been emitted which allows re-supplying those numbers of electrons by a very precisely controlled electron flood constructed so that the flood electrons can be put onto the surface from the source along a magnetically and electrostatically defined path to neutralize exactly that area of an insulator surface which was interrogated (and charged) by the focused ion beam.

Thus, the angle and time resolved particle detector (1) described in FIG. 5 is extremely versatile and can be used in conjunction with a focused keV energy ion beam to measure coincidences generated when each ion from the focused ion beam sequentially strikes a surface. The primary ion beam fluence in a micro-focused beam is inherently small (1 picoampere or less) so this ensures that, on average, only one primary ion hits the surface at any one time within a time interval of several hundred nanoseconds. Many processes happen and evolve simultaneously (within a 50 nanosecond time period after the primary ion strikes the surface as can be seen in Table 1) during the collision of each ion with the surface. All of these processes liberate energetic particles whose energy and intensity can give detailed information about the atomic composition of the surface as well as the electronic and geometric structure resulting from the arrangement of these atoms on the surface or within the near surface region.

Elemental information can be gleaned from the arrival time data and angular trajectories of electrons, photons, recoiled atoms and backscattered atoms and ions arriving in coincidence at the time-of-flight detector. As low currents are being micro-focused (e.g., roughly 150 femtoamps), a high data rate multi-anode or multi-position sensitive detector allows the beam to run continuously while acquiring time resolved data at high resolution during a 100 nanoseconds time period and with high angular resolution over a very large range of backscatter angles. For example, the acceptance cone centered on 180 degree backscatter which subtends 120 degrees is defined by a 40 millimeters diameter MCP plate placed 5 millimeters away from the sample. At these low operating currents, there would be one Helium ion striking a surface roughly every microsecond. Most electrons will travel the distance to the detector in less the 2 nanoseconds which is much less than the subsequent travel times of the backscattered ions—as seen in the Table 1 and Table 2, 20 keV $He^+$ or $Ne^+$ ions backscatter from different elements with times of flights over a 5 millimeters path length ranging from 5 nanoseconds from the heaviest elements to 10 nanoseconds for the lighter elements. The Helium backscatter times are concentrated in a relatively narrow time range because of the large difference in mass between the incident ion and the target. By contrast, Neon backscattering occurs over a much wider time range in the flight times (see Table 2).

Scattering cross sections for Helium can increase by more than an order of magnitude as the atomic mass (Z) increases from light to heavy elements. In contrast the scattering cross-section for Neon varies by roughly a factor of 3 over all elements which are heavier than Neon. The cross sections for Neon are also an order of magnitude larger than the cross sections for Helium.

Each primary ion will hit the analyte surface and subsequently create secondary electrons as they either penetrate into the surface or backscatter into the detector. The corresponding energy and angle of the backscattered ion or neutral will give information which will correspond to the surface atom present. Backscattering is normally done with a low atomic number primary ion which has a small mass like Helium. Helium will backscatter from all elements present in the surface except Hydrogen. To generate primary ion arrival timing signals, the secondary electron signal generated from the Helium ion hitting the substrate surface will be used to start a time-to-digital converter (for example, an eight channel time-to-digital converter). The travel times for the electrons can be seen below in Table 3.

TABLE 3[‡]

| Secondary Electron Energy (eV) | Average TOF (nano-seconds) | | Δ TOF (pico-seconds) | |
|---|---|---|---|---|
| | (160°-100°) towards magnetic field | (160°-100°) away from magnetic field | (160°-100°) towards magnetic field | (160°-100°) away from magnetic field |
| 2 | 0.6868 | 0.7018 | 15.6 | 29.1 |
| 4 | 0.6764 | 0.6977 | 21.7 | 40.9 |
| 6 | 0.6685 | 0.6946 | 26.2 | 49.5 |
| 8 | 0.6619 | 0.6920 | 29.9 | 56.9 |
| 10 | 0.6561 | 0.6897 | 33.0 | 63.2 |

[‡]Secondary electrons with these energies are scattered from the surface with these flight times. Note with 500 gauss field and 1000 V bias on the detector surface, gives an average TOF about 0.6826 nano-seconds and a FWHM of about 32 pico-seconds.

Figure 6:
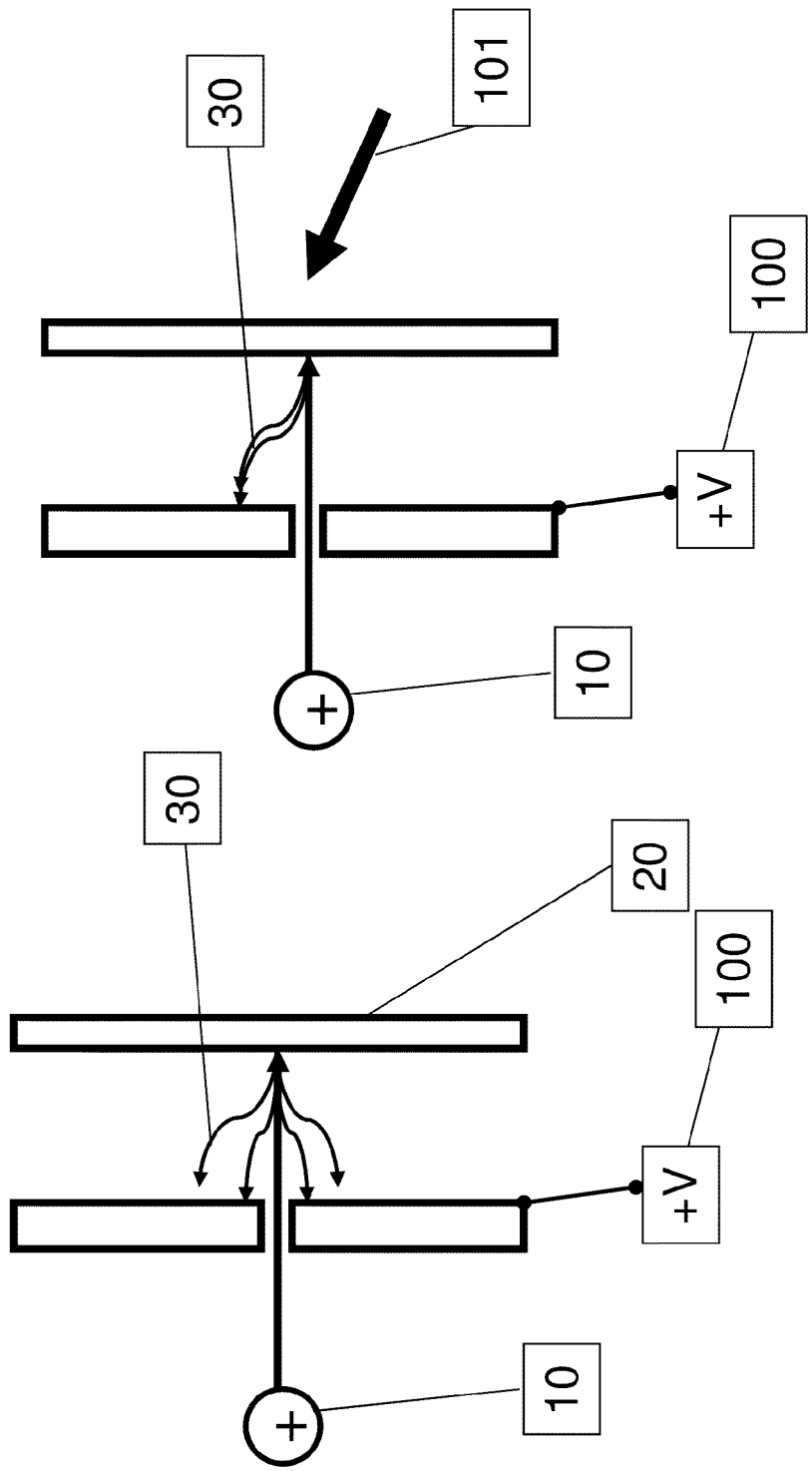
FIG. 6A shows an example of the secondary electrons ejected from the surface after primary ion collision in the presence of an electric field between sample and detector but with no magnetic field present.
FIG. 6B shows an example of the secondary electrons ejected from the surface after primary ion collision in the presence of an electric field between sample and detector with a magnetic field tilted away from the surface normal.

The secondary electrons will come off the surface at a variety of angles and energies (typically less than 10 eV), whether it is a biological sample like those used in MALDI or one of interest in the semiconductor field. A magnetic field can be used (as shown in FIG. 6B) to align the secondary electrons (30) and give them similar flight times to one specific region and area of the detector. This area or anode region will be used to generate the start signal as the primary ion strikes the sample so that the time of flight of the ions/neutrals may be measured when they strike the detector. The electrons are very easy to confine and direct along the magnetic fields compared to the magnetic fields needed to move the same ions. Using the device and methods described herein, one may direct the electrons to one region of the anode structure of the detector. It is possible to have an annular anode structure for detecting the electrons in more than one region.

FIG. 6A shows an example of the secondary electrons (30) scattering from the surface after collision in absence of a magnetic field (101) (only an electric field (100) between sample and detector). An example in FIG. 6B shows the secondary electrons ejecting from the surface after a primary ion collision with the surface in presence of a tilted magnetic field (101). After a magnetic field is applied, electrons align along the field direction, including those electrons which were initially headed away from the magnetic field direction. Timing the electrons in a mode with or without the applied magnetic field are both useful depending on the information required.

Figure 7:
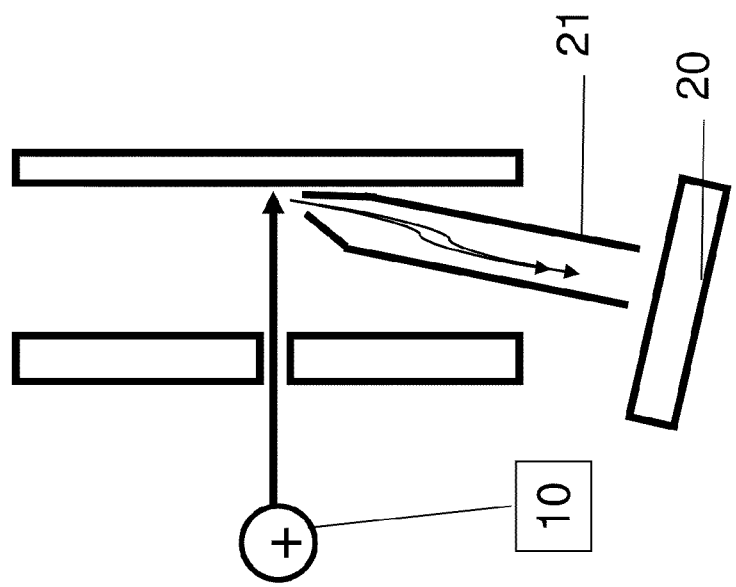
FIG. 7 shows an embodiment wherein an electrostatic lens is used to extract electrons from the point of impact and to accelerate the electrons quickly towards a second MCP multianode position sensitive detector.

FIG. 7 shows an alternate embodiment wherein an electrostatic/magnetic solenoid lens (21) is used to extract electrons from the point of impact and to accelerate the electrons quickly towards a second SED position sensitive detector (20). The SED position sensitive detector (20) is used to exclusively record secondary electrons from each primary ion impact. By keeping the distance between the entrance of the lens and the point of primary ion (10) impact less than a millimeters and using a positive bias of a few volts to a hundred volts, the timing resolution of the electrons is well under 100 picoseconds. A magnetic field along the axis of this lens may be applied by optionally activating the solenoid integral to the electrostatic lens. The solenoid is internal to the lens and its magnetic field can be shielded to eliminate magnetic field penetration outside of the lens.

Surface Crystallography of Nanocrystals.

By using time of flight backscattering, the capability of the micro-focused ion beam is enhanced not only for spatially-resolved elemental analysis but for characterizing individual crystallites whose dimensions are equal to or greater than the focal size of the beam.

Multiple Collision Sequences for Surface Recoil and Backscatter are Unraveled by Coincidence Techniques.

The energy and time-of-flight of the backscatter energy of Neon after it collides with a lighter surface bound element (e.g., Hydrogen (H), Deuterium (D), Lithium (Li), Oxygen (O) etc.) and then continues on toward the surface along with the now recoiled and energized surface bound atom can be computed for specific multiple collision sequences. For example, if Hydrogen (H) were bound to Tungsten (W) as a hydride when the Neon collides with the complex the H$^-$ backscatters from the W$^+$ while the Neon momentarily continues onward until it too hits the same W$^+$ to which the H$^-$ was bound. Thereby, two particles—one Ne and one H (neutral, negative or positive ion) are coincidentally backscattered into the detector at angles and energy which thus in co-incidence gives information about the H and the W. The scatter time of the Neon backscatter energy will be much less than the original energy (10 keV). This is because the original energy is first reduced by a collision with a light element and then further reduced by its subsequent collision with the underlying heavy element from which it then backscatters. These multiple scattering sequences broaden the backscatter distribution that is actually measured such as in FIGS. 2-3. By detecting the angle and the energy of the co-incident Neon and Hydrogen, the specific sequences which serve to broaden the backscatter spectrum can be unraveled and additional useful information can be obtained. Because the H and the Ne scatter have been measured in co-incidence only, there is one unique combination of recoil elements. The unique combination of recoil elements include: H and Ne, backscatter time (Ne from W) and the surface atom (W) to which H was bound and from which it recoiled and Ne backscattered. The flight time and recoil angle of the H can be measured and the flight time and recoil angle can be inferred by assuming the collision sequences are similar to those tabulated in Table 3. For simplicity, the energies and flight times for 180 degree light element recoil sequences and coincident Neon backscatter sequences can be calculated. These calculations can be generalized for all angles measured by the large range of backscatter angles of between 120 and 170 degrees of backscattering angles subtended by the detector.

Typically, these backscatter sequences are easily measured since the backscatter sequences are in coincidence with the electron, the angle and the energy of only two additional particles that are measured: one which is the surface recoiled light element and the other is the backscattered Ne after it has first lost energy to the particular light element and then has recoiled from the underlying heavy element. In general, much more intensity and many more coincidences are seen between the surface recoil (SR) light atom and the Ne at smaller scattering angles where the SR light atom would travel in one direction at one scatter angle with a certain energy and the Ne would travel in another direction with a particular scatter angle and energy as required by the conservation of kinetic energy and momentum (billiard ball kinematics). The coincidences may be uniquely measured and correlated with the same primary particle collision since only three particles are being detecting in co-incidence: electrons (identified by their magnetic field focusing into one small area of the detector), surface recoils (SR) (into one position on the position sensitive detector (PSD) for any one primary ion collision), and the primary multiple scattered Ne (into an opposite position and a different arrival time compared to the SR). The measurement is relatively simple and fast using a PSD because there is ample time (hundreds of nanoseconds or more on average) before the arrival of the next primary particle. This is because the two angles and energies predict a certain sequence for any two pairs of surface atoms hit by the Ne. From roughly a few thousand of these coincidence pairs, one can deduce which element is adjacent to another element and even deduce something about their geometric positions and bond lengths on the surface. This includes especially hydrogen, which can be visualized in no other way. The use of $Ne^{+2}$ (or higher m/z charge states) can also be beneficial. Prior to collision, as Ne approaches the surface, $Ne^{+2}$ liberates Auger electrons from the valence band of the solid. The energy and angle of the Auger electrons can be measured because they are in co-incidence. Furthermore, the collision of energetic Ne with light elements causes VUV emission from the light elements almost exclusively. These VUV photons can also be detected by the detector almost instantly and the resulting signal can form anywhere on the detector. The photons can be distinguished from the coincident electrons by two features: 1) the photons appear at a time slightly shorter than the arrival time of the electrons at the detector (since the electrons are traveling only at around 10% of light speed) and 2) from the location at which they are recorded by the position sensitive detector since the faster photons are diffuse while the electrons are localized into their detector area by the magnetic field. The discussion above has centered around the backscattered geometries shown in the figures in which the microprobe beam is coming directly normal to the sample surface. It is well known however, that if the beam is inclined enough relative to the surface normal, one or more detectors can be positioned to intercept any forward scattered or recoiled particles from the surface. In such a geometry the simultaneous measurement and co-incident correlation of these forward scattered particles can be made with all the other secondary particles which have already been described.

The fitting of the co-incidence data to sequential calculations is made much easier and more reliable if in-situ measurements are made to determine what elements are on the surface. The in-situ measurement may be done, for example, by MSRI (Mass Spectrometry of Recoiled Ions) XPS (X-Ray Photoelectron Spectroscopy) and/or AES (Auger Electron Spectroscopy). This can be done in real time by constructing a cylindrical mirror analyzer in which the micro-focused beam and co-axial backscatter detector are introduced co-axially through an axially symmetric curved energy analyzer which is itself equipped with a position sensitive detector. With such an analyzer, the energy and time of flight of any ionized particle which was recoiled or scattered from the surface at a scattering angle less than 120 degrees is measured and thus the mass of the ion can be calculated. These ionized particles are those leaving the surface at a very grazing elevation which would fly under the outer edge of the positions sensitive backscatter detector. Alternatively, an electrostatic time focusing analyzer such as a torodial sector which turns the focal spot into an energy resolve line or curve on a position sensitive detector can be used to also obtain simultaneous information on the forward recoiled particles. The forward recoil particles can be detected and mass analyzed by tilting the sample with respect to the beam incidence and locating such a detector to capture and energy analyze forward recoiled particles as is well known in the prior art. Timing of these recoiled ions to achieve mass can be achieved on an event by event in analogy to the backscattered spectra by correlating the arrival time of the recoiled particles with the production of secondary electrons captured in the secondary electron detector in response to the individual primary particle impingement of the surface.

While MSRI does not give elemental concentrations, it does very effectively identify the existence of an element (or an isotope) on the surface. From the MSRI intensities it is often even possible to deduce the approximate concentration of the elements present. This specific knowledge of the elements present on the surface reduces the number of possible collision partners that must be used to simulate the shape and intensity of the measured backscatter distributions.

The elemental concentration may be determined very accurately for most elements by intermittently firing a VUV laser across the surface in order to sample the secondary neutrals. The secondary neutrals have been sputtered by a number of previous Ne collisions and are slowly moving away from the surface. After each laser pulse, a linear time of flight analysis is performed or electrostatic sector analyzers may be used to obtain the elemental post-ionized mass spectrum.

Another embodiment which combines coincident backscatter, MSRI, and post-ionization, involves subtending a narrow angular range selected around a nominal scattering angle. which is chosen to have an elevation angle that allows the surface recoiled ions to both clear the surface (20) of the sample and the detector (10). The nominal scattering angle is less than 120 degrees so that the surface recoiled ions do not collide with the backscatter detector. The recoiled ions are allowed to enter along the longitudinal axis of a gridded capacitor which is intermittently pulsed by high voltage to orthogonally deflect the ions within the capacitor onto a time-of-flight detector (such as an orthogonal time-of-flight mass spectrometry (oTOFMS)). Alternatively, the surface recoils enter other time of flight analyzers such are reflectors or time and position focusing electrostatic sectors analyzers.

Step Edge Densities for Comparison with Ex-Situ LEED RHEED and X-Ray Diffraction.

The micro-focused beam incidence can be inclined to a grazing incidence so that shadow cones prohibit any primary backscattering from an atom within a smooth single crystalline surface. Thus, only the backscatter signal to arrive at the detector will be free from defects (i.e., step edges or kinks).

Imaging of Biological Surfaces During NP MALDI Matrix Implantation.

The detector can be used with large particles such as the 1 nm gold nanoparticles (AuNP). This is a very useful application of the present invention since the instrument is ideal for implanting nanoparticles into bio-tissue. The implanted nanoparticles may serve as highly efficient matrices for laser desorption of biomolecules for imaging analysis. Thus the instrument is capable of implanting nanoparticles (and simultaneously obtaining the SEM picture during implantation) into a biological surface mounted on the soft landing stage. After implantation, the sample is then transferred from the soft-landing chamber to a MALDI imaging spectrometer.

Additional embodiments of this invention are realized from its capability of accurate measurement of the exact moment of impact of the individual primary ions on a surface. This time of impact can then be used as a start signal, not only for measuring the backscattered primary particle energy distribution by time of flight, but also by using this time as the start of other time of flight analysis into other spectrometers which are attached to view line of sight particles emerging from the area between the positions sensitive detector and the sample. For example recoiled ions and elements can emerge with moderate energies and scattering angles which graze along the surface. This allows the particles to move away from the sample but miss the backscatter detector as they shoot the gap. The time of flight of these ions or neutrals relative to the time of He impact can, however, be measured by another position sensitive detector or detectors which have a line of sight view the open region between the sample and the backscatter detector. The plane of the MCPS in this line of sight detector is perpendicular to the plane of the surface and is located some few cm away from the optical axis of the ion beam. The time of arrival of these surface recoiled particles can be measured relative to the moment the individual He has been determined to strike the surface and with the known distance from the point of impact to this line of sight recoil detector the energies of surface recoil peaks can be calculated and compared to the measured distributions as described in detail in prior art. If the ion beam is tilted away from this line of sight detector then more and more of the forward scatter and recoil angles open up to the line of sight detector. Another embodiment would combine the line of sight detector with a reflectron detector as has also been shown in the prior art (Hammond).

This combination allows the ionized portion of the recoiled particles to be focused into to a reflectron time of flight mass spectrometer where their mass/charge of these ionized surface elements can be determined. This well established technique of MSRI, is discussed above. The neutral recoiled particles can pass through a hole in the end of the reflector to be detected by a line of sight detector. An alternative to the reflector mass spectrometer for this application is an orthogonal time-of-flight mass spectrometer (oTOFMS) which may be a linear or a reflectron type and whose operation is well known to skilled artisans. In this type of oTOFMS, a set of gridded parallel plate electrodes form a high voltage pulsed extraction capacitor assembly. The mass of the recoiled ions from the sample can be measured as follows: 1) the gridded capacitor is interposed between the sample and the external recoil detector, 2) the high voltage pulsed extraction capacitor assembly is oriented so that the recoiled ions from the surface traverse the capacitor assembly in a nearly parallel beam and in a direction nearly parallel to each extractor plate of the high voltage pulsed extraction capacitor assembly, 3) at measured times relative to the He impact time on the surface, a high voltage pulse is applied to the gridded extractor plates within a high voltage pulsed extraction capacitor assembly to give the ions a velocity component normal to the gridded capacitor plates. The ions are thus accelerated and pass through gridded capacitor plates and exit the high voltage pulsed extraction capacitor assembly in sideways direction toward a detector positioned facing the orthogonal plates having its face parallel to the high voltage pulsed extraction capacitor assembly, 4) the m/z of any ions is determined by timing their arrival at the linear detector relative to the time at which the a high voltage pulse is applied to the high voltage pulsed extraction capacitor assembly (this experiment can also be done where a reflector mass spectrometer is substituted in place of the linear detector). Each mass spectrum so acquired is time tagged in the data stream so that each mass spectrum from each high voltage orthogonal extraction pulse records the presence of each recoiled ion measured at a specific distance away from the point of He impact on the surface and at a specific time after the impact as defined by the time at which the high voltage orthogonal extraction pulse is applied. Thus it is possible to reconstruct from these data the velocity of each recoiled ion by plotting the mass as a function of the time after the initial primary He impact occurs at which the high voltage extractor pulse was applied to generate the mass spectrum. Since the distance from the point of He impact to the high voltage pulse extractor is known, the velocity and hence the energy distribution of each of the recoiled ions can be constructed. Moreover, it is possible to time a vacuum ultraviolet (VUV) laser to photoionize many of the more predominant neutral recoiled elements on the periodic table which are sputtered or recoiled from the surface by the primary ion. This experiment can be performed either in the traditional MSRI analyzer or in the above described oTOFMS. Using the oTOFMS the laser can be fired just above the surface some few nanosecond after the He has been determined to have impacted the surface. This will photoionize energetic neutral recoil species (more than 60% of the elements of the periodic table can be photoionized with 7.8 eV photons from a fluorine excimer laser) and the energy distributions and mass distributions of these photoionized neutrals would be determined as previously described.

Another possibility is to randomly fire a pulsed photon source such as a laser or a synchrotron light source as fast as possible through the orthogonal extraction capacitor structure to photoionize any element which has been recoiled from the surface and is present in the extractor plates during the photon pulse. This measurement does not explicitly require the use of the primary He impact timing and the mass spectra are thus correlated directly to the position of the He beam on the surface at the time of the laser firing. Another possibility is to use a continuous source of photons from a very bright continuous VUV photon source focused between the gridded capacitor plates of the high voltage pulsed extraction capacitor assembly. High voltage extraction pulses are applied as rapidly as possible to the oTOFMS. Counter-intuitively, the addition of Ne or He gas localized in the sample area (from $10^{-8}$ to $10^{-1}$ Torr; or to a few tens of mTorr pressure of He or Ne gas) as close as possible to the point of ion impact, can significantly enhance the efficiency with which these sputtered neutrals are localized and photoionized. The mass spectra of the photoionized neutrals from this method may then be correlated with the impact time of the individual primary ions as determined with the backscatter detector or the spectrum simply be correlated only with the impact position of the micro-focused beam.

Another possible embodiment uses the high accuracy timing of the primary ion impact to start the timing in many different types of time-of-flight secondary ion mass spectrometers.

Bipolar SIMS is Combined with Scattering and Secondary Electron Detection

Another embodiment of the present invention sacrifices some of the backscattered area to allow incorporation of optics which can collect nearly all low energy negatively and positively charged secondary species emitted when and energetic particle strikes the sample. Devices for extracting, counting, and timing secondary electrons liberated from a surface with a continuous ion microprobe beam while also, or optionally, performing simultaneous co-incident ion backscattering and bipolar secondary ion extraction for time-of-flight mass spectroscopy and spectrometry.

Microprobe Sources

An energetic particle beam can be micro-focused to strike the surface of a liquid or solid at a specific location—(examples of primary particles are: atomic ions (He, Ne, Ar, Kr, Xe, Ga, In, Au, Li, Na, K, Cs) or molecular ions (fullerenes, organic molecules, gold clusters, silver clusters, fast neutral atoms or molecules, photons, laser photon pulse, fission fragments, naked or near naked nuclei carrying huge numbers of positive charges (e.g., $Ag^{30+}$) all of which to varying degrees can be micro-focused for microprobe imaging applications). The focused microprobe may also be an atomic ion, molecular ion, or even an ionized nanoparticulate cluster (or, among other cluster types, ionized noble gas van der Waals clusters, molecular ion clusters, intact or fragments of large biomolecules, or solvent cluster ion or ionized aerosol). Imaging is performed by measuring the location of the focused beam on the sample and then recording the types and energies of secondary particles which are liberated from this location (examples of secondary particles are: secondary electrons (SE), Auger electrons, photons, low energy secondary ions (positive and negative), and higher energy backscattered primary or surface recoiled ions (positive and negative) and neutrals. For example, secondary electrons, H ions, carbon ions, VUV photons, x-rays can in principle be collected simultaneously either on the same or different detectors, timed and counted individually which allows their mass and/or energy to be determined, and then cross-correlated due to their co-incidence with the primary particle surface impact.

A major limitation of backscatter spectrometry is poor mass resolution and insensitivity to light elements. This limitation is partially addressed by coupling small but efficient and fast time of flight and/or magnetic secondary ion mass spectrometry (SIMS). The mass spectrometry and/or spectroscopy as well as energy analysis of secondary particles may be performed in co-incidence with one or more of certain chosen secondary particles liberated during a single primary particle collision with the surface. The secondary electrons (SE) for example are collected in a unique multi-anode position sensitive detector (secondary electron detector or SED) by which each of the multiple SE are simultaneously counted and timed on individual anodes within a few nanoseconds after the primary ion impact. This unique SED has a mechanism to scan the SE impacts over a large detector area (either by magnetics or electrostatics or a combination of both) so that new locations on the PSD are used after each primary ion impact. Thus the area of the PSD (equipped with microchannel plate electron multipliers of hybrid detectors such as MCP in combination with mesh or dynode type electron multipliers), which may have just been used to detect multiple SEs, has microseconds in which to replenish its locally depleted charge before that area is again asked to detect electrons. This innovation allows continuous SE count rates at several MHz all the while still accurately determining the time of arrival of each SE for use as a co-incidence marker of each individual ion impact.

Alternatively some of the mass and/or energy measurements may be done in co-incidence at the same time that others are being performed in an "integrating co-incidence mode". This mode is accomplished by measuring several individual co-incidence events and using combinations and specific focal properties of energy analyzers and TOF or other mass spectrometers equipped with position sensitive detections (PSD) to sort out these simultaneously detected multiple co-incidences. This embodiment for example solves the problem of how coincidences between secondary electrons, photons, and backscattered primary particles—which all occur on times scales of a few tens of nanoseconds—can be compared with other co-incident secondary ions or other secondary particles whose flight times from the point of primary ion impact on the sample to their respective detectors takes place over several microseconds. Data acquisition can sort out and assign individual secondary particle co-incidences to individual primary ion impacts onto the surface while other co-incidences can be gleaned in a data post-processing mode.

In other embodiments, the analysis of the secondary particles may be done with no regard to co-incidence wherein the secondary particle intensities are obtained by random sampling of the mass spectrometry which provides a correlation between the secondary ion and the primary ion beam positions on the sample, but not necessarily also between other co-incident events (e.g., backscattering). Another embodiment suitably combines small but moderate resolution time-of-flight mass spectroscopy (TOFMS) and magnetic sector spectrometers each equipped with position and time sensitive detection, which enables additional mass resolution of ionized secondary particles to be obtained beyond that attainable using either on their own. Thus increased mass resolution in a small package is possible and the hybrid combination furthermore solves the problem of the well known inability of time of flight to detect small ions all the while increasing mass resolution beyond that which is attainable with the small magnetic sector or small time of flight alone. Another embodiment uses the combination of all three devices: the multi-anode SED, followed by at least one magnetic sector analyzer which mass and time resolves small atomic ions and molecules, followed by an orthogonal TOFMS (oTOFMS) which time resolves the partially magnetically dispersed heavier ions onto a position sensitive detector of its own. These hybrid spectrometers have usage both in co-incidence and non-coincidence modalities. In all of the embodiments, the secondary particle extraction optics is constructed to minimally obscure the backscatter detection of ions, neutrals and photons. Thus correlations of all these signal intensities with the position of the beam on the sample are easily obtained—either in co-incidence with each other or simply in non-coincidence mode whereby signal intensities are measured as a function of beam position over an area somewhat larger than the size of the microprobe area of impact.

A further important use of the apparatus is the simultaneous correlation of negative and positive ion intensity ratios as a function of sample positions. The simultaneous detection of positive secondary ions has eluded most surface analysis techniques, yet this ratio can be very important for suggesting different spatially localized phases in which elements are found on a surface. For instance, the specific carbon ion ratio and the presence or absence of co-incident O and H ions can indicate whether a region is graphitic, diamond, fullerenic or a hydrocarbon. Similar arguments can be made for each element on the periodic table. Such a complete characterization of elemental ion ratios has awaited the development of instrumentation capable of simultaneously determining these co-incident ratios between secondary ions desorbed from very small surface areas. This new capability of inter-comparing secondary ion (and neutral) ratios from small micro-areas is now made possible by the present invention and represents a hitherto unexplored contrast mechanism for surface chemical imaging. A more complete description of some of the preferred embodiments now follows.

Time-of-Flight Start Generation from Secondary Electrons or Other Secondary Particles.

Conventional time-of-flight (TOF) mass spectrometer or ion scattering systems require a pulsed ionization method, e.g. laser, electron beam, or ion beams. If the primary beam is continuous no apparent timing reference will be available for time-of-flight measurements. An approach for finding a low-jitter electron extraction and timing reference must be developed by detecting photons, secondary electrons, or secondary ions in co-incidences with the collision of a primary ion onto an analyte surface. Alternatively, the charged secondary ionized particles can be extracted without thought to their time of formation and presented to an analyzer such as an orthogonal time of flight mass spectrometer (oTOFMS) or to an ion mobility (IM) cell coupled to an oTOFMS. In such cases, the correlation of the secondary ionized particles may be with the individual primary particle impacts or alternatively, the correlation and image acquisition may be made just with the particular position on the surface of the focused primary particle microprobe beam (i.e. all correlations between secondary ions and the particular primary particle collision are ignored and only the intensity of the secondary ions sputtered from a particular spot on the surface are measured).

Minimize Fields Along Primary Particle Beam Path

A highly focused ion beam microprobe is necessary for small spot imaging. Introduction of fields, intended or not, will potentially cause beam focus aberrations and will ultimately affect the spatial resolution of an imaging system. Extraction of particles of interest must be done with minimal effect on the primary beam focusing.

Discrimination Between Electrons, Photons, and Other Secondary Particles

Critical and unique information can be gathered from electrons, positively and negatively charged hydrogen ions, positively and negatively charged ions, and photons. The ability to identify the type of particle detected in conjunction with the TOF is key to the development of new imaging contrast mechanisms.

Size Constraint

The analyzer systems should be as small as practical consistent with the capability of also performing ion and neutral backscattering simultaneously and in coincidence with the SIMS. This requirement is essential because the dwell time of the microprobe at any one spot is determined by the longest time of flight of the secondary particles through whatever analyzer is used to determine the energy or mass of any secondary species.

Short Flight Paths and Large Energy Spreads of Ions Restrict Resolution:

The collection of TOF spectra with sufficient information requires reasonable mass and/or timing resolution and collection of a least a few tens of counts of any one type of secondary species. Minimal timing spread of all timing signals around 100 picoseconds is required to achieve useful resolutions for flight times of a few hundred nanoseconds. The need for fast (a few microseconds) collection of all information is often in conflict with the need for long flight times to obtain higher mass detection.

Figure 8:
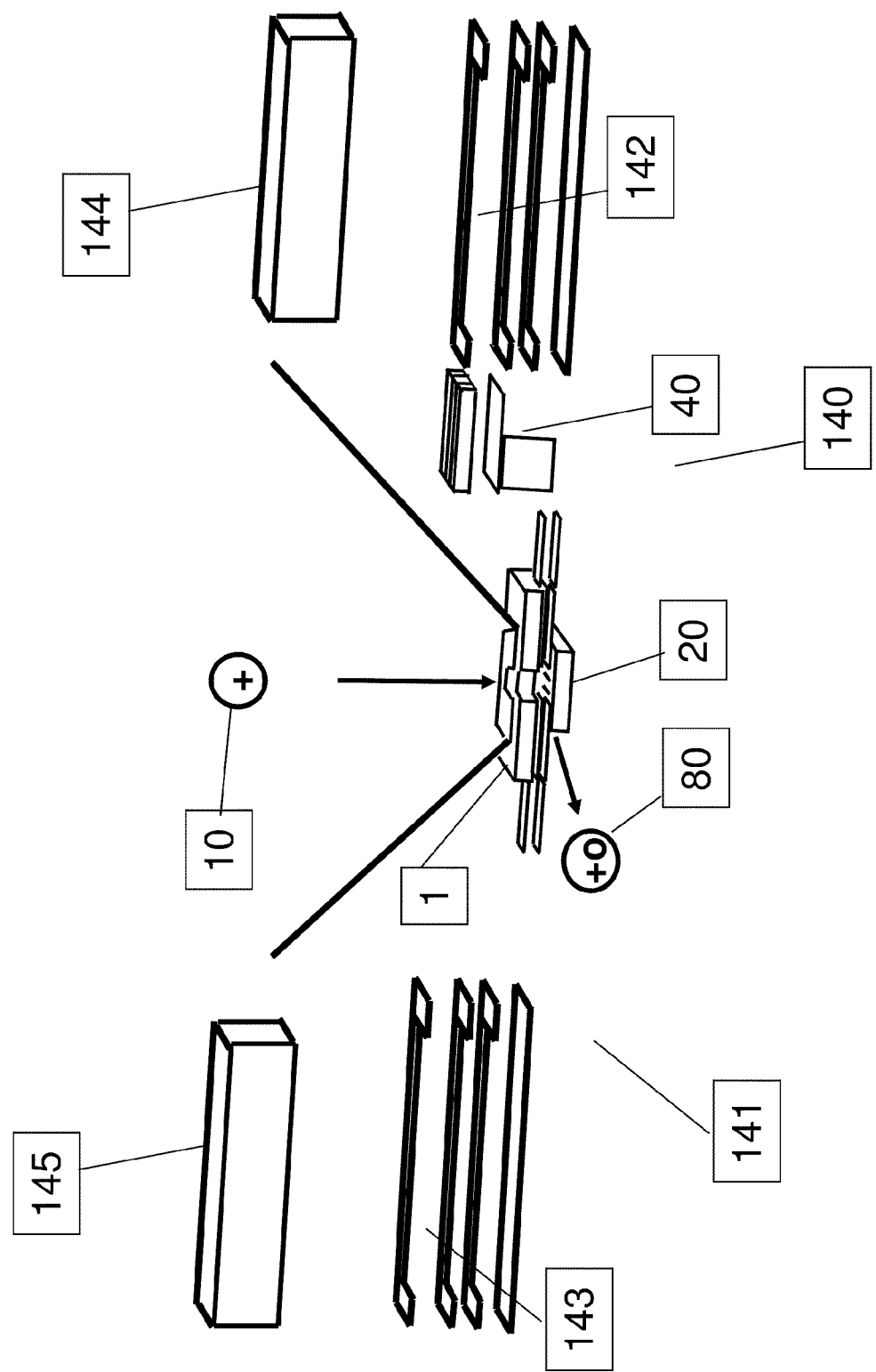
FIG. 8 shows a cross section of bipolar oTOFMS SIMS ion microprobe.

FIG. 8 shows a complete bipolar extraction spectrometer in which secondary electrons produced from the incident beam colliding with the sample can be used as a coincidence timing reference. Moreover, enhanced imaging sensitivity can be simultaneously obtained by efficient extraction of all of the secondary electrons and transporting them through a weak magnet onto a position sensitive multi-anode detector. These secondary electrons (SE)(30) are intentionally dispersed across the SED detector (40) so that they can be individually counted while maintaining a collective timing resolution of 100 picoseconds (psec) or less. Symmetrical electrodes (position, voltage polarity and magnitude) can be arranged so that the resulting field strength at the incident beam path is zero volts and positive and negative particles are extracted in opposite directions. The negative secondary particle channel (140) (electrons and negative ions move to the right in FIG. 8) will be discussed section by section while referencing FIGS. 8-12. It is understood that the discussion applies to the left channel side (141) (positive channel) if all electrode potentials and magnetic fields are reversed. A portion of the backscatter detector (1) is occluded by the extraction optics: however, by a combination of reducing the physical size of the extraction optics and making some of the optics out of transparent grids acceptance angles of between 180 and nearly 360 degree azimuthal views of the sample can still be maintained by the backscatter detector. Moreover a separate set of detectors can detect many important backscattering events which take place at very grazing exit angles (elevation angles above the surface of 5 degrees for a very atomically smooth surface) and thus miss the backscatter detector shown in FIG. 8. These grazing collisions of backscattered primary ions (80) are denoted as either + or o denoting that the backscattered particle survives as a positive ion (rarely) or as a neutral (much more likely). Surface recoils (81) can also be created by multiple collision sequences of a primary ion with individual surface atoms and some of these surface recoils can appear into this same grazing region. These recoils are predominantly neutral as well but can also be positively or negatively charged. These backscattered neutral primaries and recoils can be separated from the ions by electrostatic analyzers located out of the plane of FIG. 8 (not shown) such as a torodal sectors equipped with a high dynamic range hybrid PSD fast timing detector. The TOF of these neutrals and ions can be measured on separate detectors relative to the SED (40) timing pulse.

Figure 9:
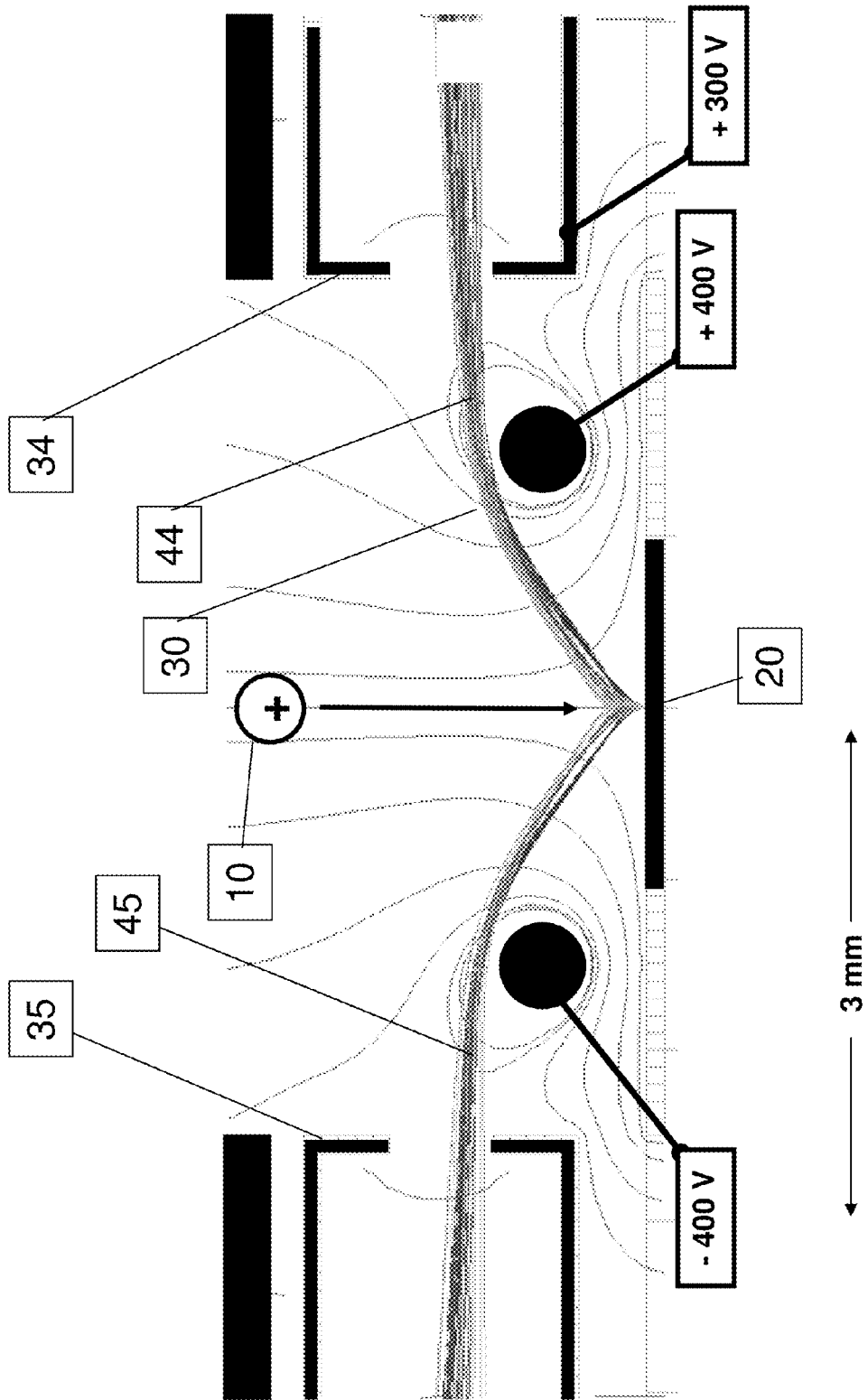
FIG. 9 shows an ion optical simulation of the negative and positive particle trajectories in extraction optics of the bipolar oTOFMS SIMS ion microprobe.

In FIG. 9, an expanded crossection view of the primary ion collision region shows the symmetric field contour lines along the direction of primary ion impact on the sample as derived from a SIMION simulation. The results are obtained in an area around the sample impact/ion extraction region (5 mm×5 mm×3 mm, L×W×H). Secondary particle energies (ions and electrons) with 1 to 5 electron volts of initial kinetic energy and with a cosine initial angular distribution are considered. As can be seen, all positive ions (45), electrons (30) and negative ions (44) within this energy and angular range are simultaneously collected in opposite directions (practically, this means that almost all ions and electrons are successfully extracted into the two analyzers). It is also an important point that the electron timing spread is almost totally dependent on extracting the SEs as quickly as possible after they are emitted from the sample, therefore, getting them accelerated to around 100 volts in a region of a few hundred microns is crucial to keeping timing spreads below 100 psec fullwidth at half maximum. In this model we are showing a wire dipole onto which +/−400 Volts is applied. In other embodiments this extraction field can be shaped by two insulating surfaces (such as a Kapton coupon) onto which a graded resistive thin film has been applied. These two surfaces are located symmetrically with respect to the centerline in place of the dipole. In other embodiments, the dipole can be replaced by two pairs of such resistive thin films on either side of the centerline and which are shaped into a sector to accelerate and provide energy filtering and two dimensional beam shaping during the acceleration process. In FIG. 9, an instrument configuration is shown in which ion extraction and focusing optics (35, 34) are orthogonal to the direction of the primary ion beam which is impinging the surface at normal incidence. Other configurations in which the sample is retracted away from the primary particle beam would allow the two opposed extraction optics (34, 35) to themselves be inclined to towards the surface normal. This configuration would assist the extraction of secondary particles. Also, the tilting of the beam away from the surface normal is also a possible geometry to enhance exposure to the forward scattering angles to other detectors.

In the embodiment of FIG. 9, the ions are bent in the plane of the figure but are angularly dispersed over a degree or more in and out of the plane of the figure. Seen also in FIG. 9 is the vertical line along the midline of the region which is also the 0 V field line. It should be noted that during the acquisition of a surface image the primary ion beam may be electrostatically scanned away from the exact axis of symmetry (geometric midline) between the positive and negative analyzers. As the ion beam is scanned away from this axis of symmetry, the extraction potentials of all the input optics can be adjusted so that the zero electrical potential surface is shifted to coincide with the new path of the scanned primary ion beam. In addition, all the potentials of the subsequent focusing and transport optics can be adjusted to compensate for the geometric asymmetry between the beam location and the midpoint between the positive and negative analyzers so that timing and mass resolutions are still maintained. In the present example, this can be adequately accomplished throughout a range of primary ion deflection of over 0.5 mm away from the geometric centerline. On the other hand, line scans in and out of the plane of the FIG. 9 can be accomplished over several mm with no required change in the analyzer extraction or transport voltages. These line scans coupled with occasional geometric shifts of the sample surface by a few nanometers relative to the extractor optics can be a very powerful way to obtain combined, SED, SIMS, and backscatter images.

Figure 10:
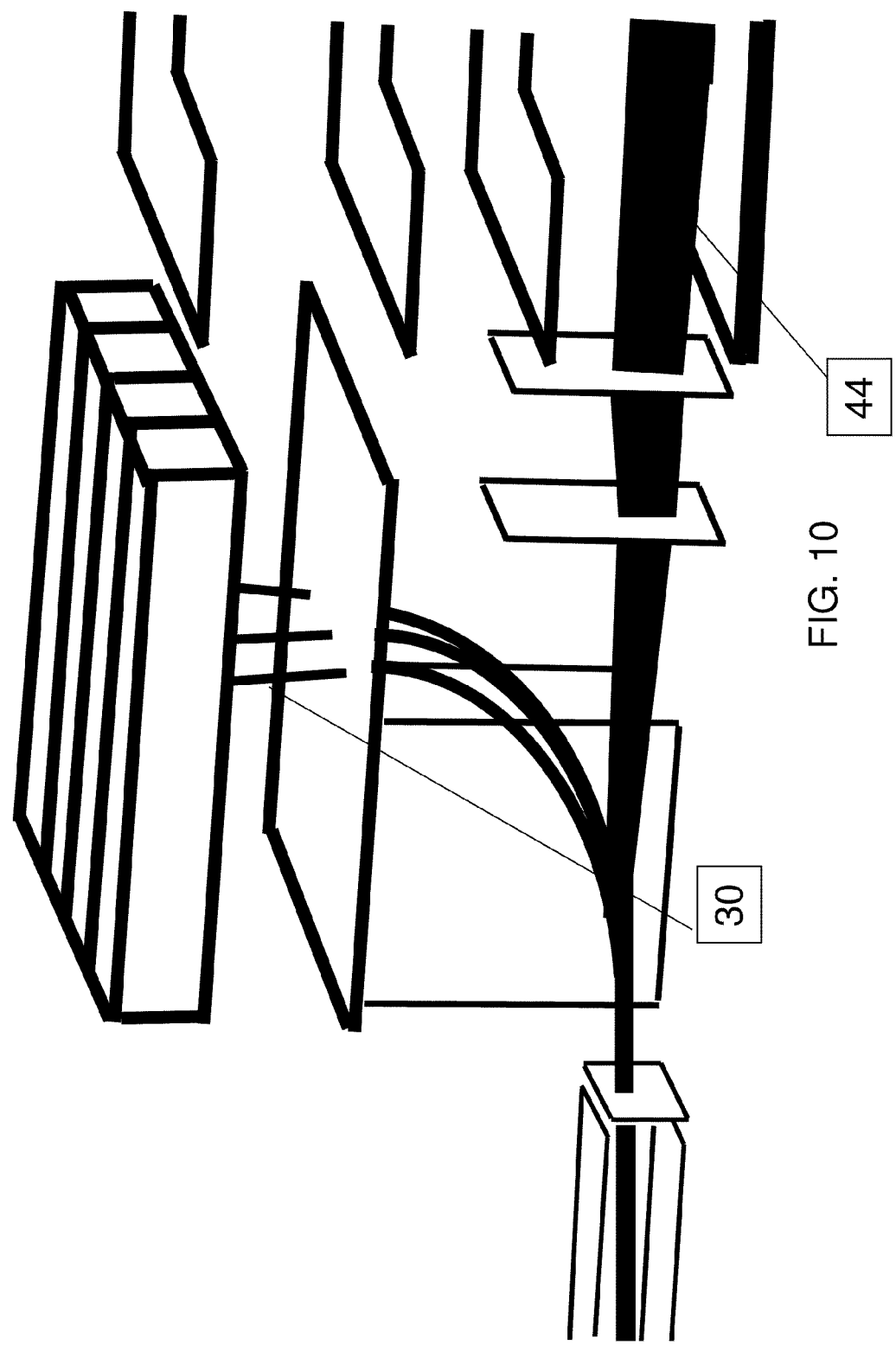
FIG. 10 shows a the special SED used within the bipolar oTOFMS SIMS ion microprobe.
Figure 11:
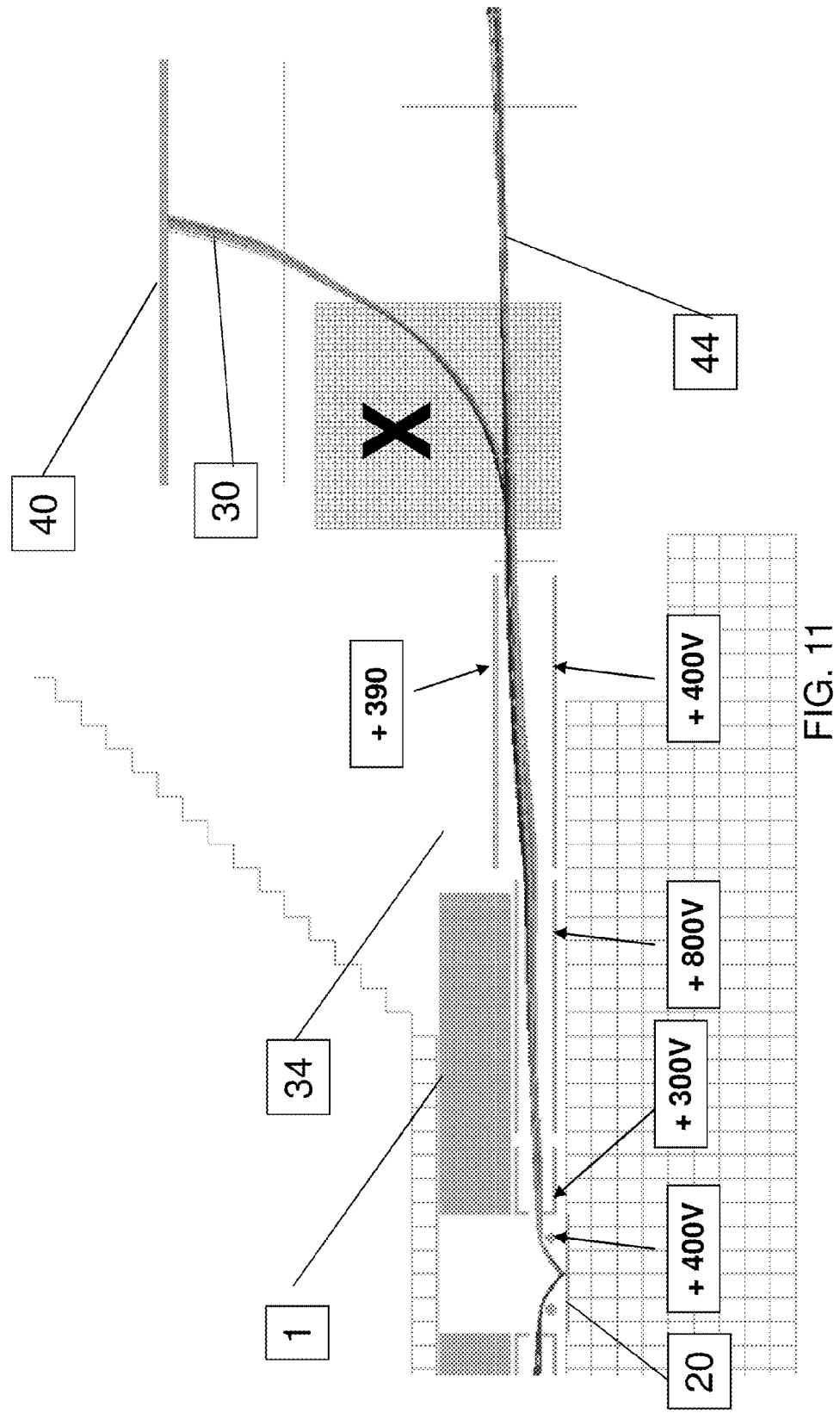
FIG. 11 shows an ion optical simulation of the magnetic filtering of the secondary electrons into the SED and the transmission of the negative secondary ions into the oTOFMS.

In FIGS. 10 and 11, after exiting the low-energy extraction optics region (35, 34) the ions and electrons travel through a series of parallel plate lens elements with approximately 2 mm spacing which allows their efficient collection (near 100%) and transport. The further important features illustrated in FIG. 9 are depicted by the electron trajectories (30) and those of the negative secondary ions (44). The application of a small magnetic field across the flight path separates the extracted secondary electrons (30) from the negative secondary ions (44) whose trajectories are scarcely affected by the weak (10-200 Gauss) magnetic field shown by an X in FIG. 11. The path of the electrons (30) will be altered while the path for the negative ions (44) will be almost unaffected. A multianode microchannel plate-based SED (40) detector (or hybrid MCP/dynode detector) will collect the diverted and focused electrons and generate a low jitter timing signal on the order of 90 picoseconds, FWHM. Several innovative features of the SED are also illustrated in FIG. 10. The electron beam covers a detector area of around 3 mm×0.3 microns. These dimensions are merely by way of example and it should be understood that others may be used. As is well known, saturation of such a small area can occur at high particle count rates. If, for example, eight electrons land in this area on an MCP detector, then although they are detected, the next grouping (arriving around 1 microsecond later) will be detected with about 50% efficiency and the next grouping may not be detected at all due to the charge depletion of the MCP channels Thus, to solve this detector saturation, the use of either a variable magnetic field or a variable electrostatic field (as provided with the electrostatic deflector grids as shown) or combinations of the two can be used to scan the electron impact area across the detector along the direction of the multianodes (depicted as stripes on the detector). Moreover, by use of the hybrid detector the depletion of charge as a function of ion count rate can be further minimized so that count rates from one to several tens of Megahertz (i.e. dynamic ranges of $10^8$). Thus the secondary electron focus on the face of the SED can be moved to more than one-hundred different locations over a period of around 100 microseconds. This gives time for any depleted MCP region to be recharged before it is called on again to detect and time subsequent SEs. This allows many MHz overall SE count rates to be obtained and conversely allows primary beam currents of between several 100 femtoamperes to 1 picoampere to be continuously used for surface imaging. Obviously, as the position of impact is changed, then the time of flight of the SEs from the impact point to the SED is changed. This change in SE flight time must be measured. This can be done by adding a meander electrode (not shown) above the multianode detector. For each SE released from the sample an electron cloud created within the MCP traverses the multanode array. Most of this electron cloud is adsorbed by the discrete anodes, while the remaining significant portion of this cloud passes between the anodes and can then be intercepted by a meander delay line—a device, well known in the art, which can establish the one dimensional position of the electron cloud along the line of the anodes. The meander is located so that a 0.5 mm pitch of the meander wires is along the line of the anodes (i.e. the meander goes back and forth orthogonally across the anodes). When the electron cloud which passes through the SED multianode array is intercepted by the meander, then the charge divides and ultimately, after the two charge groups traverse the meander to opposite ends, a timing signal can be derived from each end and the transit times relative to the recorded times of the SED timing signal from the multianodes can be recorded. The timing differences can be related to the impact position on the meander. The change in time of flight of the electrons impacting at any point along the detector can be calibrated (a look up table can be constructed for electron flight time through the SED as a function of magnetic and or electrostatic field strength so that these calibrations do not have to be performed in real time). This time of flight can be subtracted from the TOFs of any of the required TOFs of any co-incident event either in real time or in post-processing of the data. The non-diverted ions will then enter optic elements which allow the orthogonal extraction/acceleration of the ion beam.

This unique SED not only determines the transit times of the electrons from the point of primary ion surface impact to the SED but also counts the existence of individual simultaneously arriving electrons. Thus one may precisely measure the major source of current leaving the sample after each primary ion impact. In the case of insulators such as glass microscope slides, this ejection of electrons will soon cause the surface to locally charge and begin to deflect and defocus the incident ion beam. The geometry of the detectors allows a way to compensate this charging by providing neutralizing electrons onto the surface. In the positive extraction channel, a second magnetic sector can be inserted and an electron source positioned above it to generate electrons which are extracted and focused back onto the sample by the positive extraction optics. During this neutralization process, the data acquisition may need to be momentarily stopped and the voltages on the positive extraction optics optimized to desirably focus and accelerate the neutralizing electrons onto the sample.

Figure 12:
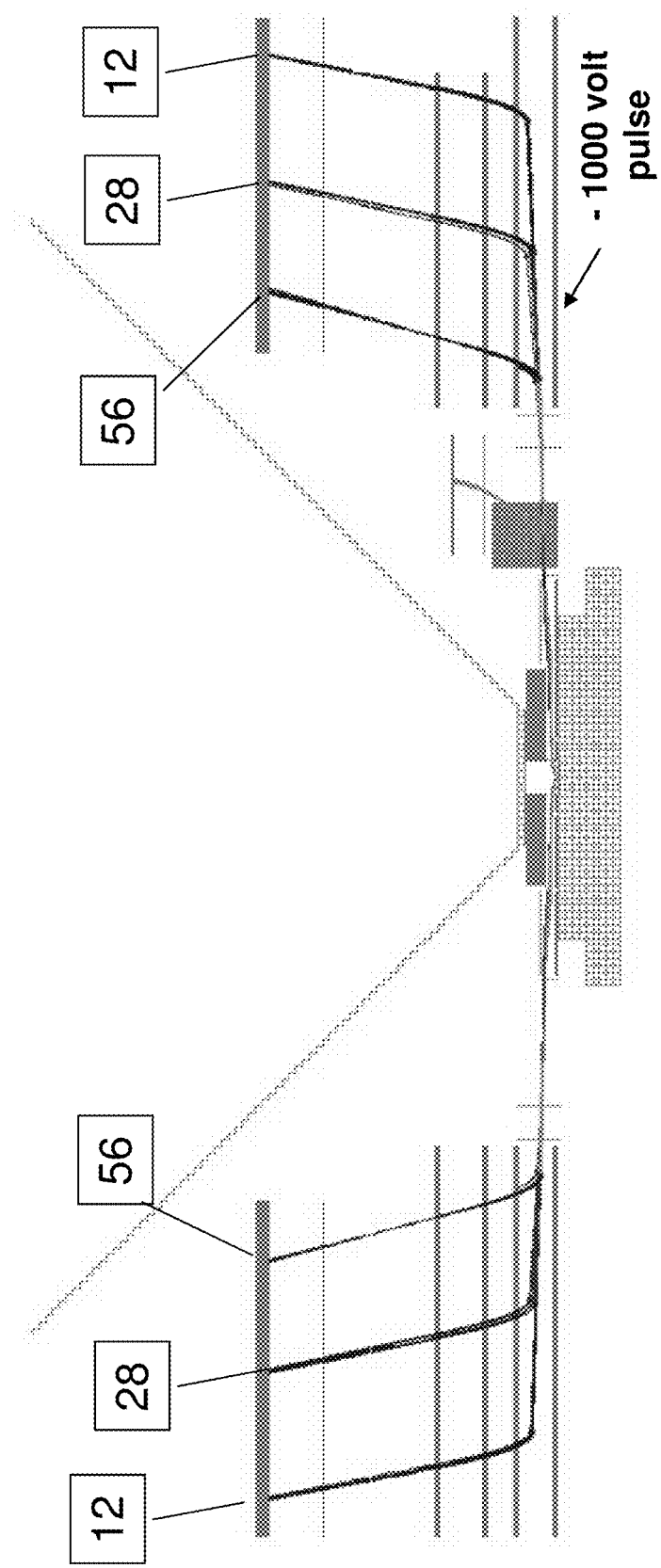
FIG. 12 shows an ion optical simulation of simultaneous positive and negative oTOFMS acquisition with one extraction pulse onto position sensitive timing detectors.

FIG. 12 illustrates the secondary ion path in a pulsed orthogonal extraction scheme. After the SE electrons are detected a delay time for applying an ortho-extraction pulse onto the appropriate plate to force the ions to go toward the secondary ion detector. FIG. 15 illustrates the case in which a delay time after the SE detection which has allowed Fe (56) to just have entered the oTOFMS while C (12) is just about to exit the oTOFMS extraction. All three test ions are detected simultaneously by PSD detectors (144, 145) attached to the negative (141) and positive (144) oTOFSIMS. The flight path of only 30 mm between the extraction plate and the detector nevertheless yields resolutions of more than 500. This resolution can be substantially increased by lengthening the flight path and also by including a small reflector stage. Moreover, by proper focusing, the secondary ions of a particular mass can be made to impact the detector with a spatial spread of a few hundred microns or less. Thus the position of impact on the oTOFMS can yield mass resolutions of several hundred. Thus the TOF given to the SI by the application of a 1000 volt extraction pulse yields resolutions of several hundred irrespective of impact position, but when the total TOF from the point of impact to the TOF detector is also measured by recording the impact position as well and additional measurement of the mass is obtained as well. Numerical deconvolution using the two different mass measurements improves the overall resolution of the oTOFMS measurement by eliminating tailing of the peaks. Essentially, a certain mass with a TOF given by the orthogonal extraction pulse cannot also impact the detector at a position accessible only by its neighboring heavier or lighter elemental ions. Of course, the oTOFMS can be used simply to determine the masses of the secondary ions ejected by the primary beam when it is stationary at a specific position without any resort to employing the SE timing signal.

However, another feature of this dual use of the SE start signal and the oTOFMS with timing and position sensitive tagging of each ion is the capability to unravel multiple co-incidences. For example if in the example shown in FIG. 12, there had been two primary ions which had hit within 500 nsec of each other and produced two well defined timing peaks on the SED, then there would potentially have been six peaks from two overlapped time of flight spectra since all two sets of identical ions could have all been in the orthogonal extraction plate when a single 1000 volt extraction pulse was applied. Each of the three different mass peaks in one spectrum would have been offset on the detector from the position of their corresponding twin by a distance at which one twin mass had flown in 500 nsec. Thus each mass peak of the second spectrum would have a twin which was precisely offset by an amount which can be predicted and used to assign each secondary ion to one or the other of the two primary ion impacts as measured by the SED. This technique becomes even more potent if the length of the detector is doubled so that more ions can simultaneously be present in the oTOFMS extraction region prior to application of the high voltage extraction pulse. In the following embodiments, we will show how a similar use of the combined SE and mass measurement can be used with a magnetic sector and with magnetic sectors combined with oTOFMS.

Alternative Solution—Combine Mattauch-Herzog Configuration with oTOFMS

Figure 13:
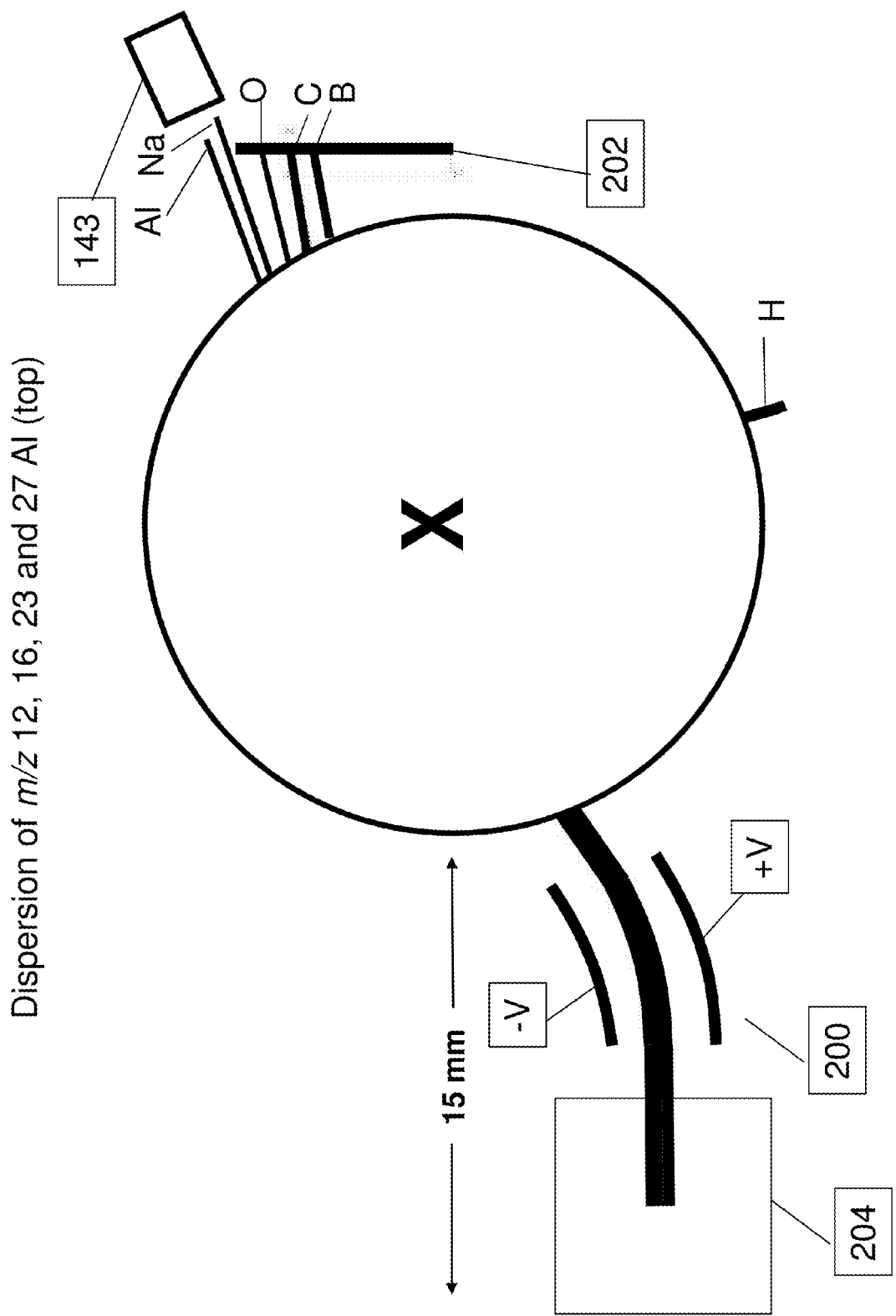
FIG. 13 shows a miniature Mattauch Herzog double focusing mass spectrometer which can be put after the ion extraction optics and before the oTOFMS.

FIG. 13 illustrates a Mattauch-Herzog double-focused mass spectrometer. One of the limitations in an oTOFMS is that light ions tend to rapidly transit the extraction region and are not therefore efficiently detected by the oTOFMS. Recent developments in mass spectrometry are occurring through the use of physically small rare earth magnets of FIG. 13 in which a Mattauch-Herzog Configuration with electrostatic sector (200), 4000 Gauss Rare earth magnetic section (201), and PSD (203). Such a small yet potent configuration is shown in FIG. 13. The same low energy extraction/steering optics is used (as shown in FIGS. 8-14) so that the secondary electrons have been deflected by a weak magnetic field and detected with the SED while the secondary ions have passed through the weak magnetic field undeflected and exited the SED (40) and proceed to enter the region (204) and from there the Mattuach Herzog spectrometer comprising an electrostatic sector (200) followed by a magnetic sector (201) which is used to focus so that mass separation onto a position sensitive detector (204) can occur (even if the PSD is non-optimally located as shown in FIG. 13). The figure also shows the flight paths for masses H, C, O, Na and Al. Notice that the Na and Al miss the PSD and enter into the oTOFMS (not shown). This topography allows simultaneous detection and mass resolution of all of these light particles with an effective duty cycle of 100%. Moreover, if we measure the timing of the arrival of the ion at the position sensitive detector relative to one of the SE timing pulses, then the same arguments previously made for the TOFMS can be made with the magnetic sector with PSD to increase the overall mass resolution of the magnetic sector MS since there are certain positions on the PSD which cannot be simultaneously occupied by two elemental ions of adjacent masses launched from the surface at the same time. Again numerical deconvolution can increase the mass resolution of this tiny mass spectrometer tremendously. Another important feature is that when using microfocused cluster or nanoparticulate ions a little known fact is that the yield of hydrogen secondary ions is high while the yield of secondary electrons is low. Thus the positive or negative hydrogen can serve as the timing marker for all other co-incidences in such cases. Moreover, detection in the magnetic sector of any of these lighter ions can be used in the same way as a co-incident timing marker—the arrival time at a specific position on the detector is uniquely defined relative to the impact position of the primary ion. Sorting of multiple light ions arriving in response to several impacts within the flight time through the sector are also facilitated by comparison to the electron arrival times at the SED.

In FIG. 13 we could use two or more PSDs—one to measure the mass range between H and B (Boron) and others to measure between C and Al. Moreover, we can envision a new hybrid by inserting the magnetic sector instrument in between the SED and the oTOFMS. The magnetic sector measures the small ions and the oTOFMS measures the heavier ions not well resolved by the magnetic sector. Moreover, multiple combinations of magnetic and oTOFMS instruments and the use of somewhat stronger and slightly larger magnets with appropriate focusing and positioning of position sensitive detectors can be envisioned while still maintaining short flight times necessary for co-incidence measurements.

Simulations indicate that it is possible to simultaneously extract secondary electrons and both positive and negative ions created from a "continuous" ion beam while generating little if any interfering fields at the source. Secondary Ion Mass Spectroscopy (SIMS) can be performed on low-energy positive and negative ions simultaneously with a mass resolution of several hundred while also collecting the higher energy backscattered ions and forward recoils in additional separate detectors. The electrons can be extracted with minimal timing spread so that a timing signal can be generated and used as an overall timing reference for other TOF data, e.g., coincident SIMS and backscatter.

Of course, the instrument can be used in applications in which the SE timing is ignored or in applications which do not attempt to determine the secondary electron yield for imaging. Such an application would involve plasma cleaning of a substrate or during plasma processing of a substrate or ozonolysis in which a resultant stream of positive and negative ions are simultaneously presented to the device through an orifice in place of the ion beam impacting upon the surface. Moreover, the device can be used in any of these modes with a post-ionizing photon source in which neutral elements or molecules can be photo-ionized and detected (since neutrals are often the charge state of the sputter secondary particle—particularly from clean metals). A particularly appropriate way to attempt these measurements is to trigger the photon source relative to the detection of the SE at the SED. Then the position sensitive techniques can be used to separate the ionized neutrals from the secondary ions. For example after Ne hits a surface the SE timing signal is determined and the secondary ions are immediately sent on their respective ways to the detector. After a few hundred nanoseconds, the photon source is fired and any neutral elements which have expanded into the vacuum are photo-ionized and extracted into the analyzers. In this way up to one in every two neutrals which are sputtered and which have a low enough ionization potential to be photo-ionized can be detected. Our spectrometer will work extremely well in conjunction with a synchrotron light source in which the high timing accuracy of the light pulse and its inherently high (kHz to MHz) pulse repetition frequency are ideally suited to photoionizing most of the neutrals. However, the addition of laser postionization to this instrument, while seemingly straightforward, is in fact problematic because of the low (few hundred Hz) repetition frequency of commercially available excimer lasers. In fact the problem with laser post-ionization in general is that even though the secondary neutrals acquire only a few eV of kinetic energy as they are sputtered from the surface, even this small kinetic energy means that most elements spend only a few tens of nanoseconds in the region above the surface. To efficiently photoionize these fast moving neutrals it is thus necessary to have the largest laser beam possible focused as close to the surface plane as possible, but without making contact.

A preferred way to post-ionize the neutrals and not seriously interfere with the collection of secondary electrons needed for the imaging and timing is to flood the area around the sample with a few tens of mTorr of helium gas. If Ne ions are used as the micro-focus probe, the addition of this small He gas pressure near the sample will not seriously degrade the focus of the keV Ne. However, the secondary neutrals will encounter a few collisions with helium gas atoms as they are ejected and will thus be present for longer times after their ejection from the surface within a volume into which the laser can be focused. This can markedly improve the efficiency with which the ejected neutrals are photoionized and detected.

The toleration of up to a few mTorr or less of He gas in an ion or photon microprobe which is focused to subnanometer dimension accomplishes another desirable feature. One can interpose a He-filled ion mobility cell between the sample and the mass spectrometer. It is known that one can use ion mobility to capture, transport and resolve secondary ions sputtered by energetic particles including atomic ions such as neon or cluster ions of various types. The disadvantages of existing commercial prior art SIMS instruments is manifold: the spectrometers are incapable of efficiently ionizing and efficiently detecting the neutral secondary particles, the mass resolution is dependent on accurately controlling the energy and time of the secondary ion ejection, and there is no discrimination between elemental and molecular ions other than by extremely high resolution mass spectrometry.

The insertion of the ion mobility along with permitting moderate He gas pressures above the sample solves this problem. The secondary ion energy distribution is rapidly cooled by the process of transporting the secondary ions which undergo multiple collisions with helium during their journey through the IM cell. Moreover, the elemental ions travel about 20% faster through the helium than do molecular ions of the same mass. Thus, distinguishing low abundance elemental ions in the presence of more predominant molecular ions is easily done with the combination of IM and oTOFMS while this feat is totally impossible with more traditional SIMS spectrometers. The placement and design of the secondary extraction optics with respect to the Ion Mobility-Mass spectrometer combination, makes it possible to rapidly transport charged secondary particles through a high vacuum enclosure (incorporating the microprobe instrument and sample) and subsequently injecting the secondary particles into a differentially pumped appendage chamber region where they are decelerated and further injected into an Ion Mobility-Mass Spectrometer. Moreover, repetitively routing the ions into multiple ion mobility channels allows a fast correlation between the output of individual IM channels and the location of the micro-focused primary particle beam on the sample. Micro-focused highly charge elements are also well known to liberate many secondary Auger electrons and secondary ions which are created by Coulomb explosion when bonding electrons are ripped from the surface.

While the previous discussion has concentrated in part on the use of secondary electrons (30) as a start detector for time of flight measurements through very small path lengths, there are many aspects of the invention which have also been emphasized as having dual use for surface analysis under higher ion beam currents (which prohibit the use of discrete timing of secondary particles with respect to secondary electron emissions). The combinations of magnetic sector analyzers (which inherently operates in an un-pulsed mode), orthogonal oTOFMS (which gets its timing for mass analysis from the application of a high voltage extraction pulse), and prior art embodiments of Ion Mobility coupled with oTOFMS (and their combinations) have been discussed. One particularly powerful combination for the analysis of the secondary ions produced at high (or low) primary ion (10) beam flux is where all of the ionized secondary particles are extracted, the negative particles are stripped of their electrons and sent to the SED (40), both negative and positive (44,45) are each optionally passed through a magnetic sector which analyzes the masses below 23 and passes any of the large ions into two "prior art" Ion Mobility oTOFMS combination which contains a deceleration and cooling region for injection of the secondary ions into a region of opposed IM cell arrays where the IM and oTOFMS analysis can be accomplished in times compatible with surface imaging. This combination also allows the SIMS ions to be separated by IM to sort elemental and molecular ions and also brings the MS/MS capability by use of various fragmentation techniques to create structural ions from SIMS ions—at present MS/MS is difficult or impossible to accomplish in modern SIMS instruments.

The backscatter and forward scatter detectors (1)—especially a forward scatter detectors combining an electrostatic energy analyzers and line of sight particle detectors—can also operate in this regime of high primary ion beam current. The prior art teaches a method and apparatus for accurately measuring the velocity of a fast particle by using a special combination of multi-channel plates (enhanced to maximize the initial number of secondary electrons created during a fast particle collision) coupled with a hybrid mesh multiplier stage to extend the dynamic range of the detector. By so doing the pulse height of the detector pulse is proportional to the velocity of the particle hitting the detector. One can of course use the electron pulse from the detector to simultaneously accurately measure the time the arrival of an ion, but coincidentally the pulse height can also be measured as well and since the pulse height is proportional to the velocity of the ion this proves useful in extending the utility of these detectors for scattering applications and indeed in mass spectrometry in general.

In the backscattering and forward scattering experiments, either a beam pulse or the secondary electron co-incident with the primary ion arrival is used to start the TDC and the backscatter event time is subsequently recorded in one of the stop channels and from this time and the known flight path the velocity is computed very accurately for each backscatter event. (The energy of the backscattered primary particle is inferred by assuming that the primary backscatters are the most prominent event so that most of the stop events occur from particles which have the mass of the primary particle). While the velocity of a backscattered particle is most accurately determined by this timing mode, there is nevertheless a fairly accurate measurement of the velocity of the particle which can be derived by measuring the detector pulse height. In fact, a potent way to calibrate the use of the detector pulse height distribution measurements for deriving the primary backscattering distributions is by acquiring both measurements simultaneously at low beam currents so that the velocities from the less accurate pulse height technique can be calibrated against the very accurate fast timing technique. As the beam current is then increased to a level where the timing technique is no longer possible (above around 500 femtoamperes to 1 picoampere), the backscattering velocity measurements can still be obtained by pulse height analysis with a calibrated level of error and uncertainty. The same arguments, apparatus, techniques and calibration approach hold as well for the forward scattering measurements made with a line of sight detector equipped with the hybrid position sensitive detector.

An especially powerful recoil mass spectrometer is thus also possible for high data rate analysis of recoiled ions by interposing an electrostatic sector analyzer (ESA) between the sample and a line of sight detector so that the line of sight detector can still view the sample through a hole in the outer electrode. This combination of an ESA with a line of sight detector is then positioned relative to the ion beam (10) incidence direction so that a desired subset of angles can be selected from a range of forward scattering angles between 85 and 5 degrees. The sector itself is uniquely equipped with a hybrid detector PSD and a position sensitive readout which is equipped to measure both time, position, and pulse height. One way to accomplish this is with an orthogonal grid of crossed wire electrodes each wire of which is electrically connected to a fast A/D converter. The pulse height and the position of impact on the PSD of the energy filtered ion can then be determined by adding and centroiding the so measured charges. Other PSD methods, such as discrete anode readouts, are well known in the art. Once the velocity, the energy, and the impact location by the combined ESA PSD are measured then one can compute the angle, mass and energy of any recoiled ion by standard techniques taught for mass spectrometry of recoiled ions (MSRI). Moreover, it is well known that scanning the ESA can be used to acquire an energy and mass resolved distribution for each recoiled ion. Mass resolutions can be much better than unity with the pulse height velocity measurement technique. Such resolution is very adequate for these measurements since the high energy collision sequence which produces the high energy recoils leaves them exiting the surface almost exclusively as pure elemental ions.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A method for analyzing a sample, comprising:
generating a continuous micro-focused beam of primary species;
directing the micro-focused beam of primary species to a sample and causing secondary species to be emitted from said sample;
detecting said secondary species, wherein the step of detecting said secondary species comprises applying opposed electric fields proximate to said sample surface, said opposed electric fields having an axis or plane of symmetry about said micro-focused beam of primary ions, said opposed electric fields simultaneously directing secondary species in the form of positive ions to a first detector and directing secondary species in the form of negative ions and electrons to a second detector;
applying a magnetic field across the flight path of negative ions and electrons to separate the electrons from the negative ions;
directing said positive ions, said negative ions or both said positive ions and said negative ions to a mass spectrometer, wherein said mass spectrometer comprises a position sensitive detector;
applying at least one of a magnetic field and an electrostatic field to scan the magnetically-separated electrons across a multianode secondary electron detector along the direction of the anodes; and
detecting the magnetically-separated electrons with the multianode secondary electron detector;
wherein said step of detecting said magnetically-separated electrons comprises counting individual electrons;
measuring a timing signal from said step of counting electrons; and
using said step of counting individual electrons to establish the time of arrival of a primary ion at said sample.

2. The method of claim 1, further comprising the steps of determining the yield of said electrons at said detector and correlating said yield with a location of impact of said primary ions with said sample.

3. The method of claim 1, wherein said mass spectrometer is a time-of-flight mass spectrometer.

4. The method of claim 3, wherein said time-of-flight mass spectrometer is a orthogonal time-of-flight mass spectrometer.

5. The method of claim 1, wherein said mass spectrometer comprises a magnetic separator.

6. The method of claim 5, wherein said magnetic separator comprises a rare earth magnet.

7. The method of claim 1, further comprising the step of intermittently firing a photon source across an area above the surface of said sample to intersect secondary species emitted from said sample.

8. The method of claim 7, further comprising applying a local gas pressure of from $10^{-1}$ to $10^{-8}$ Torr in the region above said primary species impact location on said surface of said sample.

9. The method of claim 7, further comprising the step of applying a voltage pulse to extract positive and negative ions into said first and second detectors.

10. The method of claim 1, wherein one or both of said first and second detectors comprise a mass spectrometer.

11. The method of claim 10 wherein one or both of said first and second detectors comprise an ion mobility cell.

12. The method of claim 1,
wherein said step of directing comprises directing the micro-focused beam of primary species through an aperture in a position sensitive detector to a primary species impact location on a surface of said sample thereby creating backscattered primary species and secondary species, wherein said position sensitive detector is positioned relative to the sample, such that the minimum distance between the detector plane and the impact location of said primary species on said sample is less than or equal to 100 mm; and said method further comprises:

detecting, at said position sensitive detector, the backscattered primary species and the secondary species, including arrival time and impact location of said backscattered primary species and said secondary species on said detector;

measuring a first timing signal wherein the first timing signal is generated when a first subset of secondary species strikes the position sensitive detector, said first subset of secondary species selected from the group consisting of electrons, photons, hydrogen atoms, hydrogen ions, and any combination thereof, and deriving a primary species impact time from said first timing signal, said primary species impact time being the time when said primary species impacts said sample;

measuring a second timing signal wherein the second timing signal is generated when a second subset of secondary species strikes the position sensitive detector, wherein said second subset of secondary species is any secondary species other electrons, or any combination of secondary species other than electrons; and, calculating the times of flight for the secondary species and the backscattered primary species with a time of flight analysis using said first timing signal, said primary species impact location, said second timing signal, said impact position on said position sensitive detector, and a known geometry between said sample and said position sensitive detector.

13. The method of claim 12, further comprising the step of adjusting the micro-focused primary species beam fluence such that about only one particle hits the sample surface within a period between 100 nanoseconds and 10 microseconds.

14. The method of claim 13, further comprising the step of adjusting the micro-focused ion beam fluence such that about only one particle hits the sample surface within about 1 microsecond.

15. The method of claim 12, further comprising the step of accelerating the secondary species from the sample to the detector by applying an electric field between the sample and the detector.

16. The method of claim 12, wherein said position sensitive detector is positioned relative to the sample, such that the minimum distance between the detector plane and the impact location of said primary species on said sample is less than or equal to 80 mm.

17. The method of claim 16, wherein said position sensitive detector is positioned relative to the sample, such that the minimum distance between the detector plane and the impact location of said primary species on said sample is less than or equal to 50 mm.

18. The method of claim 17, wherein said position sensitive detector is positioned relative to the sample, such that the minimum distance between the detector plane and the impact location of said primary species on said sample is less than or equal to 25 mm.

19. The method of claim 18, wherein said position sensitive detector is positioned relative to the sample, such that the minimum distance between the detector plane and the impact location of said primary species on said sample is less than or equal to 10 mm.

20. The method of claim 12, wherein said position sensitive detector is positioned relative to the sample, such that the minimum distance between the detector plane and the impact location of said primary species on said sample is 5 mm.

21. The method of claim 12, wherein said position sensitive detector is positioned relative to the sample, such that the minimum distance between the detector plane and the impact location of said primary species on said sample is 3 mm.

22. The method of claim 12, further comprising the steps of determining the yield of said secondary species and correlating said yield with a location of impact of said primary ions with said sample.

23. The method of claim 22, further comprising the step of directing at least a portion of said secondary species to a mass spectrometer.

24. The method of claim 23, wherein said mass spectrometer is a time-of-flight mass spectrometer.

25. The method of claim 24, wherein said time-of-flight mass spectrometer is a orthogonal time-of-flight mass spectrometer.

26. An apparatus, comprising:
a source of a micro-focused beam of primary species;
a surface for holding, rotating, and titling a sample, said surface positioned such that flow from said source is incident upon said sample;
a plurality of electrodes, proximate to said sample surface and configured to produce two opposed electric fields to simultaneously direct secondary species in the form of positive ions in a first direction and to direct secondary species in the form of negative ions and electrons in a second direction, wherein said first and second directions are symmetrically opposed to one another about the primary ion beam;
a magnetic field source to separate electrons from negative ions;
a first detector positioned to detect said positive ions travelling in said first direction, a second detector positioned to detect said negative ions travelling in said second direction;
at least one position sensitive detector, said position sensitive detector (PSD) positioned to detect backscattered primary and secondary species deflected by the plurality of electrodes and the magnetic field source;
a multianode detector configured to detect the separated electrons; and
a field source configured to generate at least one of a magnetic field and an electrostatic field to scan the separated electrons across a plurality of anodes of the multianode detector along the direction of the anodes.

27. The apparatus of claim 26, wherein one or both of said first and second detectors comprise a mass spectrometer.

28. The apparatus of claim 27, wherein said mass spectrometer is an orthogonal time-of-flight mass spectrometer, a magnetic spectrometer, or a combination of an orthogonal time-of-flight mass spectrometer and a magnetic spectrometer.

29. The apparatus of claim 28, wherein said magnetic spectrometer comprises a rare earth magnet.

30. The apparatus of claim 26, wherein one or both of said first and second detectors comprise an ion mobility cell.

31. The apparatus of claim 26, further comprising a photon source positioned to emit photons across an area above the surface of said sample.

32. The apparatus of claim 31, further comprising a gas doser positioned to apply from $10^{-1}$ to $10^{-8}$ Torr of gas pressure in the region above said primary species impact location on said surface of said sample.

33. The apparatus of claim 26, further comprising an electron source positioned between said first detector and said sample.

34. The method of claim 1, further comprising simultaneously counting scattered primary ions and neutrals, recoiled surface atoms and ions, positive SIMS, neutral SIMS, and post-ionized positive neutrals.

35. The apparatus of claim 26, wherein the apparatus simultaneously counts scattered primary ions and neutrals, recoiled surface atoms and ions, positive SIMS, neutral SIMS, and post-ionized positive neutrals.

36. The method of claim 1, wherein scanning the separated electrons comprises scanning the separated electrons across a multianode secondary electron detector to prevent charge depletion of any one anode of a plurality of anodes of the multianode secondary electron detector.

37. The apparatus of claim 26, wherein the field source is configured to scan the separated electrons across the multianode detector to prevent charge depletion of any one anode of the plurality of anodes of the multianode detector.

* * * * *